United States Patent

Nabika

(10) Patent No.: US 6,528,671 B1
(45) Date of Patent: Mar. 4, 2003

(54) TRANSITION METAL COMPOUND, ADDITION POLYMERIZATION CATALYST COMPONENT, ADDITION POLYMERIZATION CATALYST AND PROCESS FOR PRODUCTION OF OLEFIN POLYMER

(75) Inventor: Masaaki Nabika, Ichihara (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/672,306

(22) Filed: Sep. 29, 2000

(30) Foreign Application Priority Data

Oct. 5, 1999 (JP) ............................................. 11-283993

(51) Int. Cl.$^7$ ............................ C07F 17/00; B01J 31/00
(52) U.S. Cl. ...................... 556/20; 502/103; 502/117; 502/152; 502/155; 526/127; 526/160; 526/161; 526/352; 526/943
(58) Field of Search ........................... 556/20; 502/103, 502/117, 152, 155; 526/127, 160, 161, 352, 943

(56) References Cited

U.S. PATENT DOCUMENTS

| 4,542,199 A | 9/1985 | Kaminsky et al. .......... 526/160 |
| 6,063,879 A | 5/2000 | Stephan et al. .............. 526/127 |
| 6,355,744 B1 * | 3/2002 | von Haken Spence et al. .. 526/127 |

FOREIGN PATENT DOCUMENTS

| WO | 9500526 | 1/1995 |
| WO | 9600734 | 1/1996 |
| WO | 9600742 | 1/1996 |

* cited by examiner

Primary Examiner—Porfirio Nazario-Gonzalez
(74) Attorney, Agent, or Firm—Stevens, Davis, Miller & Mosher, L.L.P.

(57) ABSTRACT

A transition metal compound obtained by reacting (a) a transition metal compound represented by the following general formula (1) with (b) a conjugated or non-conjugated diene in the presence of a compound (c) selected from the group consisting of alkyllithiums, alkali metals, alkali metal hydrides and Grignard compounds, and a transition metal compound represented by the following general formula (2), an addition polymerization catalyst obtained by contacting the above-mentioned transition metal compound (2) with a co-catalyst for activation, and a method for producing an olefin polymer with the addition polymerization catalyst.

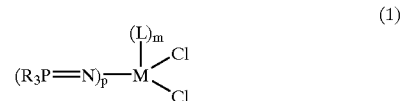

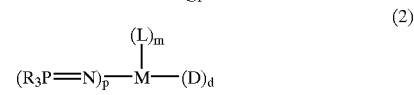

(In the general formula (1) or (2), M represents a titanium atom, zirconium atom or hafnium atom, L represents a group having an aromatic π electron and is connected to M via the π electron, D represents a conjugated or non-conjugated diene, R represents a hydrogen atom, alkyl group, aralkyl group, aryl group or substituted silyl group, all R's may be the same or different, d is 1 or 2, p is 1 or 2, m is 0 or 1, and the sum of p and m is 2.).

4 Claims, No Drawings

TRANSITION METAL COMPOUND, ADDITION POLYMERIZATION CATALYST COMPONENT, ADDITION POLYMERIZATION CATALYST AND PROCESS FOR PRODUCTION OF OLEFIN POLYMER

BACKGROUND OF THE INVENTION

1. Field of the Invention

The present invention relates to a transition metal compound suitable as an addition polymerization catalyst component, an addition polymerization catalyst, and a process for producing an olefin polymer.

2. Description of the Relates Arts

A lot of reports have been made previously regarding a process for producing an olefin polymer using a transition metal compound such as a metallocene complex or the like. For example, a process for producing an olefin polymer using a metallocene complex and aluminoxane, has been reported in JP-A-58-19309. Further, regarding an olefin polymerization using a transition metal compound in which a diene compound is a ligand, a bridging type monocyclopentadienyl complex in which titanium has a formal oxidation number of II is disclosed in WO95/00526, and a bridging type monocyclopentadienyl complex as described above having a metallacycle structure in which titanium has a formal oxidation number of IV, is disclosed in WO96/00734. On the other hand, regarding a non-bridged type monocyclopentadienyl complex, JP-A-10-502396 discloses that a monocyclopentadienyl titanium (diphenylbutadiene) complex is useful in stereoregular polymerization of styrene by combining with various co-catalysts, and, regarding a polymerization using a monocyclopentadienyl titanium complex in which a phosphineimine is a ligand, JP-A-10-338706 discloses that a polymer of high molecular weight can be produced by conducting solution polymerization of an olefin at a temperature of 80° C. or more. However, these processes were not admitted as satisfactory from the standpoint of polymerization activity.

SUMMARY OF THE INVENTION

The object of the present invention is to provide a transition metal compound useful as an addition polymerization catalyst component which can exhibit high activity, an addition polymerization catalyst component composed of the above-mentioned transition metal compound, a highly active addition polymerization catalyst prepared by using the above-mentioned transition metal compound, and a process for efficiently producing an olefin polymer using the above-mentioned addition polymerization catalyst.

Namely, the present invention relates to a transition metal compound obtained by reacting a transition metal compound (a) represented by the following general formula (1) with (b) a conjugated diene or non-conjugated diene in the presence of (c) a compound selected from the group consisting of an alkyllithium, alkali metal, hydrogenated substance of an alkali metal, and Grignard compound, and to a transition metal compound represented by the following general formula (2). Further, the present invention relates to an addition polymerization catalyst composed of the above-mentioned transition metal compound, an addition polymerization catalyst obtained by contacting the above-mentioned transition metal compound with a co-catalyst for activation, and a method for producing an olefin polymer using the above-mentioned addition polymerization catalyst.

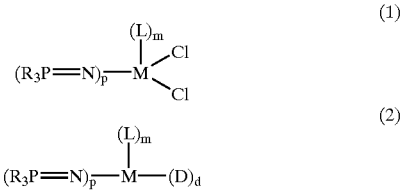

(wherein, in the general formula (1) or (2), M represents a titanium atom, zirconium atom or hafnium atom; L represents a group having an aromatic π electron and is connected to M via the π electron; D represents a conjugated diene or non-conjugated diene; R represents a hydrogen atom, alkyl group, aralkyl group, aryl group or substituted silyl group, and all R's may be the same or different; d is 1 or 2; p is 1 or 2, m is 0 or 1; and the sum of p and m is 2.).

The present invention will be illustrated further in detail below.

DETAILED DESCRIPTION OF THE INVENTION

(A) Transition Metal Compound

The transition metal compound (A) of the present invention is a transition metal compound obtained by reacting a transition metal compound (a) represented by the following general formula (1) with a conjugated diene or non-conjugated diene (b) in the presence of a compound (c) selected from the group consisting of alkyllithiums, alkali metals, hydrogenated substances of an alkali metal and Grignard compounds.

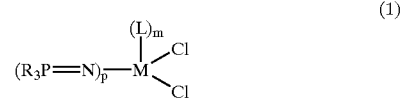

M in the transition metal compound represented by the above-mentioned general formula (1) represents a titanium atom, zirconium atom or hafnium atom, and particularly preferably a titanium atom.

Examples of the group represented by L having an aromatic π electron and is connected to M via the π electron include an $\eta^5$-cyclopentadienyl group, $\eta^5$-methylcyclopentadienyl group, $\eta^5$-dimethylcyclopentadienyl group, $\eta^5$-trimethylcyclopentadienyl group, $\eta^5$-tetramethylcyclopentadienyl group, $\eta^5$-ethylcyclopentadienyl group, $\eta^5$-n-propylcyclopentadienyl group, $\eta^5$-isopropylcyclopentadienyl group, $\eta^5$-n-butylcyclopentadienyl group, $\eta^5$-sec-butylcyclopentadienyl group, $\eta^5$-tert-butylcyclopentadienyl group, $\eta^5$-n-pentylcyclopentadienyl group, $\eta^5$-neopentylcyclopentadienyl group, $\eta^5$-n-hexylcyclopentadienyl group, $\eta^5$-n-octylcyclopentadienyl group. $\eta^5$-phenylcyclopentadienyl group, $\eta^5$-naphthylcyclopentadienyl group, $\eta^5$-trimethylsilylcyclopentadienyl group, $\eta^5$-triethylsilylcyclopentadienyl group, $\eta^5$-tert-butyldimethylsilylcyclopentadienyl group, $\eta^5$-indenyl group, $\eta^5$-methylindenyl group, $\eta^5$-dimethylindenyl group, $\eta^5$-ethylindenyl group, $\eta^5$-n-propylindenyl group, $\eta^5$-isopropylindenyl group, $\eta^5$-n-butylindenyl group, $\eta^5$-sec-butylindenyl group, $\eta^5$-tert-butylindenyl group, $\eta^5$-n-pentylindenyl group, $\eta^5$-neopentylindenyl group, $\eta^5$-n-hexylindenyl group, $\eta^5$-n-octylindenyl group, $\eta^5$-n-decylindenyl group, $\eta^5$-phenylindenyl group, $\eta^5$-methylphenylindenyl group, $\eta^5$-naphthylindenyl group, $\eta^5$-trimethylsilylindenyl group, $\eta^5$-triethylsilylindenyl group, $\eta^5$-tert-butyldimethylsilylindenyl group, $\eta^5$-tetrahydroindenyl group, $\eta^5$-fluorenyl group, $\eta^5$-methylfluorenyl group, $\eta^5$-dimethylfluorenyl group, $\eta^5$-ethylfluorenyl group, $\eta^5$-diethylfluorenyl group, $\eta^5$-n-propylfluorenyl group, $\eta^5$-di-n-propylfluorenyl group, $\eta^5$-isopropylfluorenyl group, $\eta^5$-diisopropylfluorenyl group, $\eta^5$-n-butylfluorenyl group, $\eta^5$-sec-butylfluorenyl group, $\eta^5$-tert-butylfluorenyl group, $\eta^5$-di-n-butylfluorenyl group, $\eta^5$-di-sec-butylfluorenyl group, $\eta^5$-di-tert-butylfluorenyl group, $\eta^5$-n-pentylfluorenyl group, $\eta^5$-neopentylfluorenyl group, $\eta^5$-n-hexylfluorenyl group, $\eta^5$-n-octylfluorenyl group, $\eta^5$-n-decylfluorenyl group, $\eta^5$-n-dodecylfluorenyl group, $\eta^5$-phenylf luorenyl group, $\eta^5$-di-phenylfluorenyl group, $\eta^5$-methylphenylfluorenyl group, $\eta^5$-naphthylfluorenyl group, $\eta^5$-trimethylsilylfluorenyl group, $\eta^5$-bis-trimethylsilylfluorenyl group, $\eta^5$-triethylsilylfluorenyl group, $\eta^5$-tert-butyldimethylsilylfluorenyl group and the like, and preferable examples thereof include an $\eta^5$-cyclopentadienyl group, $\eta^5$-methylcyclopentadienyl group, $\eta^5$-tert-butylcyclopentadienyl group, $\eta^5$-tetramethylcyclopentadienyl group, $\eta^5$-indenyl group or $\eta^5$-fluorenyl group.

R in the general formula (1) represents a hydrogen atom, alkyl group, aralkyl group, aryl group or substituted silyl group, and all R's may be the same or different.

The alkyl group in the substituent R is preferably an alkyl group having 1 to 20 carbon atoms, and more preferably an alkyl group having 4 to 10 carbon atoms, and examples thereof include a methyl group, ethyl group, n-propyl group, isopropyl group, n-butyl group, sec-butyl group, tert-butyl group, n-pentyl group, neopentyl group, tert-pentyl group, cyclopentyl group, n-hexyl group, cyclohexyl group, n-octyl group, n-decyl group, n-dodecyl group, n-pentadecyl group, n-eicosyl group and the like, and more preferably a n-butyl group, tert-butyl group, neopentyl group, cyclopentyl group, tert-pentyl group and cyclohexyl group.

Any of these alkyl groups may also be substituted with a halogen atom such as a fluorine atom, chlorine atom, bromine atom or iodine atom. Examples of the alkyl group having 1 to 20 carbon atoms substituted with a halogen atom include a fluoromethyl group, difluoromethyl group, trifluoromethyl group, chloromethyl group, dichloromethyl group, trichloromethyl group, bromomethyl group, dibromomethyl group, tribromomethyl group, iodomethyl group, diiodomethyl group, triiodomethylgroup, fluoroethylgroup, difluoroethyl group, trifluoroethyl group, tetrafluoroethyl group, pentafluoroethyl group, chloroethyl group, dichloroethyl group, trichloroethyl group, tetrachloroethyl group, pentachloroethyl group, bromoethyl group, dibromoethyl group, tribromoethyl group, tetrabromoethyl group, pentabromoethyl group, perfluoropropyl group, perfluorobutyl group, perfluoropentyl group, perfluorohexyl group, perfluorooctyl group, perfluorododecyl group, perfluoropentadecyl group, perfluoroeicosyl group, perchloropropyl group, perchlorobutyl group, perchloropentyl group, perchlorohexyl group, perchlorooctyl group, perchlorododecyl group, perchloropentadecyl group, perchloroeicosyl group, perbromopropyl group, perbromobutyl group, perbromopentyl group, perbromohexyl group, perbromooctyl group, perbromododecyl group, perbromopentadecyl group, perbromoeicosyl group and the like.

Any of these alkyl groups may also be partially substituted with an alkoxy group such as a methoxy groups ethoxy group or the like, an aryloxy group such as a phenoxy group or the like, or an aralkyloxy group such as a benzyloxy group or the like.

The aralkyl group in the substituent R is preferably an aralkyl group having 7 to 20 carbon atoms, and examples thereof include a benzyl group, (2-methylphenyl)methyl group, (3-methylphenyl)methyl group, (4-methylphenyl)methyl group, (2,3-dimethylphenyl)methyl group, (2,4-dimethylphenyl)methyl group, (2,5-dimethylphenyl)methyl group, (2,6-dimethylphenyl)methyl group, (3,4-dimethylphenyl)methyl group, (3,5-dimethylphenyl)methyl group, (2,3,4-trimethylphenyl)methyl group, (2,3,5-trimethylphenyl)methyl group, (2,3,6-trimethylphenyl)methyl group, (3,4,5-trimethylphenyl)methyl group, (2,4,6-trimethylphenyl)methyl group, (2,3,4,5-tetramethylphenyl)methyl group, (2,3,4,6-tetramethylphenyl)methyl group, (2,3,5,6-tetramethylphenyl)methyl group, (2,3,4,5-group, (ethylphenyl)methyl group, (n-propylphenyl)methyl group, (isopropylphenyl)methyl group, (n-butylphenyl)methyl group, (sec-butylphenyl)methyl group, (tert-butylphenyl)methyl group, (n-pentylphenyl)methyl group, (neopentylphenyl)methyl group, (n-hexylphenyl)methyl group, (n-octylphenyl)methyl group, (n-decylphenyl)methyl group, (n-tetradecylphenyl)methyl group, naphthylmethyl group, anthracenylmethyl group and the like, and a benzyl group is more preferable.

Any of these aralkyl groups may also be partially substituted with a halogen atom such as a fluorine atom, chlorine atom, bromine atom or iodine atom, an alkoxy group such as a methoxy group, ethoxy group or the like, an aryloxy group such as a phenoxy group or the like, or an aralkyloxy group such as a benzyloxy group or the like.

The aryl group in the substituent R is preferably an aryl group having 6 to 20 carbon atoms, and more preferably an aryl group having 7 to 18 carbon atoms. Examples thereof include a phenyl group, 2-tolyl group, 3-tolyl group, 4-tolyl group, 2,3-xylyl group, 2,4-xylyl group, 2,5-xylyl group, 2,6-xylyl group, 3,4-xylyl group, 3,5-xylyl group, 2,3,4-trimethylphenyl group, 2,3,5-trimethylphenyl group, 2,3,6-trimethylphenyl group, 2,4,6-trimethylphenyl group, 3,4,5-trimethylphenyl group, 2,3,4,5-tetramethylphenyl group, 2,3,4,6-tetramethylphenyl group, 2,3,5,6-tetramethylphenyl group, pentamethylphenyl group, ethylphenyl group, n-propylphenyl group, isopropylphenyl group, n-butylphenyl group, sec-butylphenyl group, tert-butylphenyl group, n-pentylphenyl group, neopentylphenyl group, n-hexylphenyl group, n-octylphenyl group,; n-decylphenyl group, n-dodecylphenyl group, n-tetradecylphenyl group, naphthyl group, anthracenyl group and the like, and more preferably a tolyl group, xylyl group, tert-butylphenyl group, di-tert-butylphenyl group, tert-butylmethylphenyl group or di-tert-butylmethylphenyl group.

Any of these aryl groups may also be partially substituted with a halogen atom such as a fluorine atom, chlorine atom, bromine atom or iodine atom, an alkoxy group such as a methoxy group, ethoxy group or the like, an aryloxy group such as a phenoxy group or the like, or an aralkyloxy group such as a benzyloxy group or the like.

The substituted silyl group in the substituent R is a silyl group substituted with a hydrocarbon group, and examples of the hydrocarbon group include alkyl groups having 1 to 10 carbon atoms such as a methyl group, ethyl group, n-propyl group, isopropyl group, n-butyl group, sec-butyl group, tert-butyl group, isobutyl group, n-pentyl group, n-hexyl group, cyclohexyl group and the like, aryl groups such as a phenyl group and the like. Examples of the substituted silyl group having 1 to 20 carbon atoms include mono-substituted silyl groups having 1 to 20 carbon atoms such as a methylsilyl group, ethylsilyl group, phenylsilyl group and the like, di-substituted silyl groups having 2 to 20 carbon atoms such as a dimethylsilyl group, diethylsilyl group, diphenylsilyl group and the like, tri-substituted silyl groups having 3 to 20 carbon atoms such as a triemthylsilyl group, triethylsilyl group, tri-n-propylsilyl group, triisopropylsilyl group, tri-n-butylsilyl group, tri-sec-butyl silyl group, tri-tert-butylsilyl group, tri-isobutylsilyl group, tert-butyldimethylsilyl group, tri-n-pentylsilyl group, tri-n-hexylsilyl group, tricyclohexylsilyl group, triphenylsilyl group and the like, and preferable examples thereof include a trimethylsilyl group, tert-butyldimethylsilyl group and triphenylsilyl group.

Any of these substituted silyl groups may also be partially substituted with a halogen atom such as a fluorine atom, chlorine atom, bromine atom or iodine atom, an alkoxy group such as a methoxy group, ethoxy group or the like, an aryloxy group such as a phenoxy group or the like, or an aralkyloxy group such as a benzyloxy group or the like.

R in the general formula (1) is more preferably an alkyl group, substituted aryl group or substituted silyl group, particularly preferably a methyl group, ethyl group, tert-butyl group, neopentyl group, cyclopentyl group, cyclohexyl group, methoxyphenyl group or trimethylsilyl group.

m in the general formula (1) is 0 or 1, p is 1 or 2, and the sum of m and p is 2. Particularly preferably, both of m and p represent 1.

The transition metal compound (A) of the present invention is a transition metal compound obtained by reacting a transition metal compound(a) represented by the above-described general formula (1) with a conjugated diene or non-conjugated diene(b) in the presence of a compound (c) selected from the group consisting of alkyllithiums, alkali metals, alkali metal hydrides and Grignard compounds.

The transition metal compound (a) represented by the general formula (1) is produced, for example, by a method described in Organometallics, Vol. 18, pp. 1116–1118 (1999) or J. Organometallic Chem., Vol. 159, pp. 47–52 (1978) or the like. The specific examples of the transitionmetal compound (a) are those obtained by replacing the groups corresponding to —(D)p of the specific examples of the transition metal compound represented by the general formula (2) described below with $Cl_2$ (dichloride).

The conjugated diene or non-conjugated diene (b) is preferably a conjugated diene or non-conjugated diene having 4 to 40 carbon atoms and more preferably a conjugated diene, and specific examples thereof include butadiene, 1,3-pentadiene, isoprene, 1,3-hexadiene, 2,4-hexadiene, 2,3-dimethylbutadiene, 1,3-heptadiene, 2,4-heptadiene, 2,3-dimethyl-1,3-pentadiene, 1,3-octadiene, 2,4-octadiene, 3,5-octadiene, 3,4-dimethyl-2,4-hexadiene, 5,5-dimethyl-1,3-hexadiene, 2,2,7,7-tetramethyl-3,5-octadiene, 2,4,5,7-tetramethyl-3,5-octadiene, 1-phenylbutadiene, 2-phenylbutadiene, 1,4-diphenylbutadiene, 2,3-diphenylbutadiene and the like, and butadiene, 2,4-hexadiene or 1,4-diphenylbutadiene is particularly preferable.

The compound (c) is a compound selected from the group consisting of alkyllithiums, alkali metals, alkali metal hydrides, and Grignard compounds.

The alkyllithium is preferably an alkyllithium having 1 to 10 carbon atoms, and more preferably methyllithium, ethyllithium, n-propyllithium, n-butyllithium or tert-butyllithium.

Examples of the alkyl metal include lithium, sodium, potassium and the like, and lithium or sodium is preferable.

Examples of the alkali metal hydride include lithium hydride, sodium hydride, potassium hydride and the like, and lithium hydride or sodium hydride is preferable.

The Grignard compound is preferably a compound represented by the general formula R'MgX' (wherein, Mg represents a magnesium atom, R' represents a hydrocarbon group having 1 to 20 carbon atoms, and X' represents a halogen atom). Specific examples of R' include alkyl, aryl, aralkyl and alkenyl groups having 1 to 20 carbon atoms such as a methyl group, ethyl group, n-propyl group, isopropyl group, n-butyl group, sec-butyl group, tert-butyl group, isopentyl group, n-hexyl group, n-octyl group, 2-ethylhexyl group, phenyl group, benzyl group and the like. The Grignard compound is particularly preferably isopropylmagnesium chloride.

The amount of the conjugated diene or non-conjugated diene (b) used is usually 1 to 5-fold by mole based on the amount of the transition metal compound (a) used in the reaction.

When the amount of the conjugated diene or non-conjugated diene (b) used is extremely smaller than that of the transition metal compound (a), the production yield of the transition metal compound (A) may lower. Too large amount of the conjugated diene or non-conjugated diene (b) is uneconomical and not preferable. The amount thereof is preferably from 1 to 3-fold by mol, and more preferably from 1 to 1.5-fold by mol.

The amount used of the compound(c) selected from the group consisting of alkyllithiums, alkali metals, alkali metal hydrides, and Grignard compounds (hereinafter, sometimes abbreviated as "compound (c)") is usually from 1-fold to 10-fold mol based on the amount of the transition metal compound (a) used in the present reaction.

When the amount of the compound (c) used is extremely smaller than that of the transition metal compound (a) used, the production yield of the transition metal compound (A) may lower. Too large amount of the compound (c) is uneconomical and not preferable. The use amount thereof is preferably from 1.5 to 3-fold by mol, and more preferably from 1.8 to 2.5-fold by mol.

Regarding the addition order of reagents in the present reaction, the compound (c) may be added to a mixed solution of the transition metal compound (a) and the conjugated or non-conjugated diene (b), or the transition metal compound (a) may be added to a mixed solution of the conjugated diene or non-conjugated diene (b) and the compound (c). Alternatively, the reverse order is permissible.

The reaction is usually carried out in a solvent inert to the reagents. Examples of this solvent include aromatic hydrocarbon solvents such as benzene, toluene, xylene, mesitylene and the like, aliphatic hydrocarbon solvents such as pentane, hexane, heptane, octane and the like, ether solvents such as diethyl ether, tetrahydrofuran and the like. These solvents are used alone or in combination of two or more, and the use amount thereof is usually from 1 to 200-fold by weight, preferably from 3 to 50-fold by weight based on the use amount of the transition metal compound (a).

The reaction temperature is not particularly restricted, and the reaction is conducted at a temperature preferably from −100° C. to the boiling point of a solvent used in the reaction, and more preferably from −80 to 150° C. and lower than the boiling point of the solvent. Industrially, lower temperature is not preferable, and the reaction is conducted at a temperature preferably from −20 to 80° C. and lower than the boiling point of the solvent.

The transition metal compound (A) of the present invention is obtained by the above-mentioned reaction, and for example, when butadiene is used as the conjugated diene or non-conjugated diene (b), a transition metal compound (A1) in which the transition metal atom M has a formal oxidation number of II and a transition metal compound (A2) in which the transition metal atom M has a formal oxidation number of IV as described below are usually obtained.

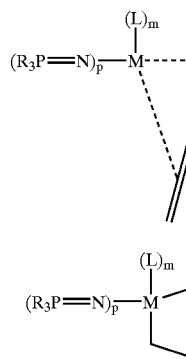

The configuration of butadiene in (A1) is s-trans or s-cis configuration.

The transition metal compound (A) in the present invention is, as one embodiment, a transition metal compound represented by the following general formula (2)

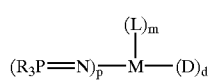

Wherein, M, L, R, p and m are as defined in the above-mentioned transition metal compound represents by the general formula (1), and D represents the above-described conjugated diene or non-conjugated diene (b), and d is 1 or 2.

Specific examples of the transition metal compound represented by the general formula (2) include (cyclopentadienyl)(trimethylphosphineimine)(butadiene)titanium, (cyclopentadienyl)(trimethylphosphineimine)(1,3-pentadiene)titanium, (cyclopentadienyl)(trimethylphosphineimine)(isoprene)titanium, (cyclopentadienyl)(trimethylphosphineimine)(1,3-hexadiene)titanium, (cyclopentadienyl)(trimethylphosphineimine)(2,4-hexadiene)titanium, (cyclopentadienyl)(trimethylphosphineimine)(2,3-dimethylbutadiene)titanium, (cyclopentadienyl)(trimethylphosphineimine)(1,3-heptadiene)titanium, (cyclopentadienyl)(trimethylphosphineimine)(2,4-heptadiene)titanium, (cyclopentadienyl)(trimethylphosphineimine)(2,3-dimethyl-1,3-pentadiene)titanium, (cyclopentadienyl)(trimethylphosphineimine)(1,3-octadiene)titanium, (cyclopentadienyl)(trimethylphosphineimine)(2,4-octadiene)titanium, (cyclopentadienyl)(trimethylphosphineimine)(3,5-octadiene)titanium, (cyclopentadienyl)(trimethylphosphineimine)(3,4-dimethyl-2,4-hexadiene)titanium, (cyclopentadienyl)(trimethylphosphineimine)(5,5-dimethyl-1,3-hexadiene)titanium, (cyclopentadienyl)(trimethylphosphineimine)(2,7-dimethyl-3,5-octadiene)titanium, (cyclopentadienyl)(trimethylphosphineimine)(4,5-dimethyl-3,5-octadiene)titanium, (cyclopentadienyl)(trimethylphosphineimine)(2,2,7,7-tetramethyl-3,5-octadiene)titanium, (cyclopentadienyl)(trimethylphosphineimine)(2,4,5,7-tetramethyl-3,5-octadiene)titanium, (cyclopentadienyl)(trimethylphosphineimine)(1-phenylbutadiene)titanium, (cyclopentadienyl)(trimethylphosphineimine)(2-phenylbutadiene)titanium, (cyclopentadienyl)(trimethylphosphineimine)(1,4-diphenylbutadiene)titanium, (cyclopentadienyl)(trimethylphosphineimine)(2,3-diphenylbutadiene)titanium, (cyclopentadienyl)(triethylphosphineimine)(butadiene)titanium, (cyclopentadienyl)(triethylphosphineimine)(1,3-pentadiene)titanium, (cyclopentadienyl)(triethylphosphineimine)(isoprene)titanium, (cyclopentadienyl)(triethylphosphineimine)(1,3-hexadiene)titanium, (cyclopentadienyl)(triethylphosphineimine)(2,4-hexadiene)titanium, (cyclopentadienyl)(triethylphosphineimine)(2,3-dimethylbutadiene)titanium, (cyclopentadienyl)(triethylphosphineimine)(1,3-heptadiene)titanium, (cyclopentadienyl)(triethylphosphineimine)(2,4-heptadiene)titanium, (cyclopentadienyl)(triethylphosphineimine)(2,3-dimethyl-1,3-pentadiene)titanium, (cyclopentadienyl)(triethylphosphineimine)(1,3-octadiene)titanium, (cyclopentadienyl)(triethylphosphineimine)(2,4-octadiene)titanium, (cyclopentadienyl)(triethylphosphineimine)(3,5-octadiene)titanium, (cyclopentadienyl)(triethylphosphineimine)(3,4-dimethyl-2,4-hexadiene)titanium, (cyclopentadienyl)(triethylphosphineimine)(5,5-dimethyl-1,3-hexadiene)titanium, (cyclopentadienyl)(triethylphosphineimine)(2,7-dimethyl-3,5-octadiene)titanium, (cyclopentadienyl)(triethylphosphineimine)(4,5-dimethyl-3,5-octadiene)titanium, (cyclopentadienyl)(triethylphosphineimine)(2,2,7, 7-tetramethyl-3,5-octadiene)titanium, (cyclopentadienyl)(triethylphosphineimine)(2,4,5,7-tetramethyl-3,5-octadiene)titanium, (cyclopentadienyl)(triethylphosphineimine)(1-phenylbutadiene)titanium, (cyclopentadienyl)(triethylphosphineimine)(2-phenylbutadiene)titanium, (cyclopentadienyl)(triethylphosphineimine)(1,4-diphenylbutadiene)titanium, (cyclopentadienyl)(triethylphosphineimine)(2,3-diphenylbutadiene)titanium, (cyclopentadienyl)(tri-n-propylphosphineimine)(butadiene)titanium, (cyclopentadienyl)(tri-n-propylphosphineimine)(1,3-pentadiene)titanium, (cyclopentadienyl)(tri-n-propylphosphineimine)(isoprene)titanium, (cyclopentadienyl)(tri-n-propylphosphineimine)(1,3-hexadiene)titanium, (cyclopentadienyl)(tri-n-propylphosphineimine)(2,4-hexadiene)titanium, (cyclopentadienyl)(tri-n-propylphosphineimine)(2,3-dimethylbutadiene)titanium, (cyclopentadienyl)(tri-n-propylphosphineimine)(1,3-heptadiene)titanium, (cyclopentadienyl)(tri-n-propylphosphineimine)(2,4-heptadiene)titanium, (cyclopentadienyl)(tri-n-propylphosphineimine)(2,3-dimethyl-1,3-pentadiene)titanium, (cyclopentadienyl)(tri-n-propylphosphineimine)(1,3-octadiene)titanium, (cyclopentadienyl)(tri-n-propylphosphineimine)(2,4-octadiene)titanium, (cyclopentadienyl)(tri-n-propylphosphineimine)(3,5-octadiene)titanium, (cyclopentadienyl)(tri-n-propylphosphineimine)(3,4-dimethyl-2,4-hexadiene)titanium, (cyclopentadienyl)(tri-n-propylphosphineimine)(5,5-dimethyl-1,3-hexadiene)titanium, (cyclopentadienyl)(tri-n-propylphosphineimine)(2,7-dimethyl-3,5-octadiene)titanium, (cyclopentadienyl)(tri-n-propylphosphineimine)(4,5-dimethyl-3,5-octadiene)titanium, (cyclopentadienyl)(tri-n-propylphosphineimine)(2,2,7,7-tetramethyl-3,5-octadiene)titanium, (cyclopentadienyl)(tri-n-propylphosphineimine)(2,4,5,7-tetramethyl-3,5-octadiene)titanium, (cyclopentadienyl)(tri-n-propylphosphineimine)

(1-phenylbutadiene)titanium, (cyclopentadienyl)(tri-n-propylphosphineimine)(2-phenylbutadiene)titanium, (cyclopentadienyl)(tri-n-propylphosphineimine)(1,4-diphenylbutadiene)titanium, (cyclopentadienyl)(tri-n-propylphosphineimine)(2,3-diphenylbutadiene)titanium, (cyclopentadienyl)(triisopropylphosphineimine)(butadiene)titanium, (cyclopentadienyl)(triisopropylphosphineimine)(1,3-pentadiene)titanium, (cyclopentadienyl)(triisopropylphosphineimine)(isoprene)titanium, (cyclopentadienyl)(triisopropylphosphineimine)(1,3-hexadiene)titanium, (cyclopentadienyl)(triisopropylphosphineimine)(2,4-hexadiene)titanium, (cyclopentadienyl)(triisopropylphosphineimine)(2,3-dimethylbutadiene)titanium, (cyclopentadienyl)(triisopropylphosphineimine)(1,3-heptadiene)titanium, (cyclopentadienyl)(triisopropylphosphineimine)(2,4-heptadiene)titanium, (cyclopentadienyl)(triisopropylphosphineimine)(2,3-dimethyl-1,3-pentadiene)titanium, (cyclopentadienyl)(triisopropylphosphineimine)(1,3-octadiene)titanium, (cyclopentadienyl)(triisopropylphosphineimine)(2,4-octadiene)titanium, (cyclopentadienyl)(triisopropylphosphineimine)(3,5-octadiene)titanium, (cyclopentadienyl)(triisopropylphosphineimine)(3,4-dimethyl-2,4-hexadiene)titanium, (cyclopentadienyl)(triisopropylphosphineimine)(5,5-dimethyl-1,3-hexadiene)titanium, (cyclopentadienyl)(triisopropylphosphineimine)(2,7-dimethyl-3,5-octadiene)titanium, (cyclopentadienyl)(triisopropylphosphineimine)(4,5-dimethyl-3,5-octadiene)titanium, (cyclopentadienyl)(triisopropylphosphineimine)(2,2,7,7-tetramethyl-3,5-octadiene)titanium, (cyclopentadienyl)(triisopropylphosphineimine)(2,4,5,7-tetramethyl-3,5-octadiene)titanium, (cyclopentadienyl)(triisopropylphosphineimine)(1-phenylbutadiene)titanium, (cyclopentadienyl)(triisopropylphosphineimine)(2-phenylbutadiene)titanium, (cyclopentadienyl)(triisopropylphosphineimine)(1,4-diphenylbutadiene)titanium, (cyclopentadienyl)(triisopropylphosphineimine)(2,3-diphenylbutadiene)titanium, (cyclopentadienyl)(tri-n-butylphosphineimine)(butadiene)titanium, (cyclopentadienyl)(tri-n-butylphosphineimine)(1,3-pentadiene)titanium, (cyclopentadienyl)(tri-n-butylphosphineimine)(isoprene)titanium, (cyclopentadienyl)(tri-n-butylphosphineimine)(1,3-hexadiene)titanium, (cyclopentadienyl)(tri-n-butylphosphineimine)(2,4-hexadiene)titanium, (cyclopentadienyl)(tri-n-butylphosphineimine)(2,3-dimethylbutadiene)titanium, (cyclopentadienyl)(tri-n-butylphosphineimine)(1,3-heptadiene)titanium, (cyclopentadienyl)(tri-n-butylphosphineimine)(2,4-heptadiene)titanium, (cyclopentadienyl)(tri-n-butylphosphineimine)(2,3-dimethyl-1,3-pentadiene)titanium, (cyclopentadienyl)(tri-n-butylphosphineimine)(1,3-octadiene)titanium, (cyclopentadienyl)(tri-n-butylphosphineimine)(2,4-octadiene)titanium, (cyclopentadienyl)(tri-n-butylphosphineimine)(3,5-octadiene)titanium, (cyclopentadienyl)(tri-n-butylphosphineimine)(3,4-dimethyl-2,4-hexadiene)titanium, (cyclopentadienyl)(tri-n-butylphosphineimine)(5,5-dimethyl-1,3-hexadiene)titanium, (cyclopentadienyl)(tri-n-butylphosphineimine)(2,7-dimethyl-3,5-octadiene)titanium, (cyclopentadienyl)(tri-n-butylphosphineimine)(4,5-dimethyl-3,5-octadiene)titanium, (cyclopentadienyl)(tri-n-butylphosphineimine)(2,2,7,7-tetramethyl-3,5-octadiene)titanium, (cyclopentadienyl)(tri-n-butylphosphineimine)(2,4,5,7-tetramethyl-3,5-octadiene)titanium, (cyclopentadienyl)(tri-n-butylphosphineimine)(1-phenylbutadiene)titanium, (cyclopentadienyl)(tri-n-butylphosphineimine)(2-phenylbutadiene)titanium, (cyclopentadienyl)(tri-n-butylphosphineimine)(1,4-diphenylbutadiene)titanium, (cyclopentadienyl)(tri-n-butylphosphineimine)(2,3-diphenylbutadiene)titanium, (cyclopentadienyl)(tri-sec-butylphosphineimine)(butadiene)titanium, (cyclopentadienyl)(tri-sec-butylphosphineimine)(1,3-pentadiene)titanium, (cyclopentadienyl)(tri-sec-butylphosphineimine)(isoprene)titanium, (cyclopentadienyl)(tri-sec-butylphosphineimine)(1,3-hexadiene)titanium, (cyclopentadienyl)(tri-sec-butylphosphineimine)(2,4-hexadiene)titanium, (cyclopentadienyl)(tri-sec-butylphosphineimine)(2,3-dimethylbutadiene)titanium, (cyclopentadienyl)(tri-sec-butylphosphineimine)(1,3-heptadiene)titanium, (cyclopentadienyl)(tri-sec-butylphosphineimine)(2,4-heptadiene)titanium, (cyclopentadienyl)(tri-sec-butylphosphineimine)(2,3-dimethyl-1,3-pentadiene)titanium, (cyclopentadienyl)(tri-sec-butylphosphineimine)(1,3-octadiene)titanium, (cyclopentadienyl)(tri-sec-butylphosphineimine)(2,4-octadiene)titanium, (cyclopentadienyl)(tri-sec-butylphosphineimine)(3,5-octadiene)titanium, (cyclopentadienyl)(tri-sec-butylphosphineimine)(3,4-dimethyl-2,4-hexadiene)titanium, (cyclopentadienyl)(tri-sec-butylphosphineimine)(5,5-dimethyl-1,3-hexadiene)titanium, (cyclopentadienyl)(tri-sec-butylphosphineimine)(2,7-dimethyl-3,5-octadiene)titanium, (cyclopentadienyl)(tri-sec-butylphosphineimine)(4,5-dimethyl-3,5-octadiene)titanium, (cyclopentadienyl)(tri-sec-butylphosphineimine)(2,2,7,7-tetramethyl-3,5-octadiene)titanium, (cyclopentadienyl)(tri-sec-butylphosphineimine)(2,4,5,7-tetramethyl-3,5-octadiene)titanium, (cyclopentadienyl)(tri-sec-butylphosphineimine)(1-phenylbutadiene)titanium, (cyclopentadienyl)(tri-sec-butylphosphineimine)(2-phenylbutadiene)titanium, (cyclopentadienyl)(tri-sec-butylphosphineimine)(1,4-diphenylbutadiene)titanium, (cyclopentadienyl)(tri-sec-butylphosphineimine)(2,3-diphenylbutadiene)titanium, (cyclopentadienyl)(triisobutylphosphineimine)(butadiene)titanium, (cyclopentadienyl)(triisobutylphosphineimine)(1,3-pentadiene)titanium, (cyclopentadienyl)(triisobutylphosphineimine)(isoprene)titanium, (cyclopentadienyl)(triisobutylphosphineimine)(1,3-hexadiene)titanium, (cyclopentadienyl)(triisobutylphosphineimine)(2,4-hexadiene)titanium, (cyclopentadienyl)(triisobutylphosphineimine)(2,3-dimethylbutadiene)titanium, (cyclopentadienyl)(triisobutylphosphineimine)(1,3-heptadiene)titanium, (cyclopentadienyl)(triisobutylphosphineimine)(2,4-heptadiene)titanium, (cyclopentadienyl)(triisobutylphosphineimine)(2,3-dimethyl-1,3-pentadiene)titanium, (cyclopentadienyl)(triisobutylphosphineimine)(1,3-octadiene)titanium, (cyclopentadienyl)(triisobutylphosphineimine)(2,4-octadiene)titanium, (cyclopentadienyl)(triisobutylphosphineimine)(3,5-octadiene)titanium, (cyclopentadienyl)(triisobutylphosphineimine)(3,4-dimethyl-2,4-hexadiene)titanium, (cyclopentadienyl)(triisobutylphosphineimine)(5,5-dimethyl-1,3-hexadiene)titanium, (cyclopentadienyl)(triisobutylphosphineimine)(2,7-dimethyl-3,5-octadiene)titanium, (cyclopentadienyl)(triisobutylphosphineimine)(4,5-dimethyl-3,5-octadiene)titanium, (cyclopentadienyl)(triisobutylphosphineimine)(2,2,7,7-tetramethyl-3,5-octadiene)titanium, (cyclopentadienyl)(triisobutylphosphineimine)(2,4,5,7-tetramethyl-3,5-octadiene)titanium, (cyclopentadienyl)(triisobutylphosphineimine)(1-phenylbutadiene)titanium, (cyclopentadienyl)(triisobutylphosphineimine)(2-phenylbutadiene)titanium, (cyclopentadienyl)(triisobutylphosphineimine)(1,4-diphenylbutadiene)titanium, (cyclopentadienyl)(triisobutylphosphineimine)(2,3-diphenylbutadiene)titanium, (cyclopentadienyl)(tri-tert-butylphosphineimine)(butadiene)titanium, (cyclopentadienyl)(tri-tert-butylphosphineimine)(1,3-pentadiene)titanium, (cyclopentadienyl)(tri-tert-butylphosphineimine)(isoprene)titanium, (cyclopentadienyl)(tri-tert-butylphosphineimine)(1,3-hexadiene)titanium, (cyclopentadienyl)(tri-tert-butylphosphineimine)(2,4-hexadiene)titanium, (cyclopentadienyl)(tri-tert-butylphosphineimine)(2,3-dimethylbutadiene)titanium, (cyclopentadienyl)(tri-tert-butylphosphineimine)(1,3-heptadiene)titanium, (cyclopentadienyl)(tri-tert-butylphosphineimine)(2,4-heptadiene)titanium, (cyclopentadienyl)(tri-tert-butylphosphineimine)(2,3-dimethyl-1,3-pentadiene)titanium, (cyclopentadienyl)(tri-tert-butylphosphineimine)(1,3-octadiene)titanium, (cyclopentadienyl)(tri-tert-butylphosphineimine)(2,4-octadiene)titanium, (cyclopentadienyl)(tri-tert-butylphosphineimine)(-3,5-octadiene)titanium, (cyclopentadienyl)(tri-tert-butylphosphineimine)(3,4-dimethyl-2,4-hexadiene)titanium, (cyclopentadienyl)(tri-tert-butylphosphineimine)(5,5-dimethyl-1,3-hexadiene)titanium, (cyclopentadienyl)(tri-tert-butylphosphineimine)(2,7-dimethyl-3,5-octadiene)titanium, (cyclopentadienyl)(tri-tert-butylphosphineimine)(4,5-dimethyl-3,5-octadiene)titanium, (cyclopentadienyl)(tri-tert-butylphosphineimine)(2,2,7,7-tetramethyl-3,5-octadiene)titanium, (cyclopentadienyl)(tri-tert-butylphosphineimine)(2,4,5,7-tetramethyl-3,5-octadiene)titanium, (cyclopentadienyl)(tri-tert-butylphosphineimine)(1-phenylbutadiene)titanium, (cyclopentadienyl)(tri-tert-butylphosphineimine)(2-phenylbutadiene)titanium, (cyclopentadienyl)(tri-tert-butylphosphineimine)(1,4-diphenylbutadiene)titanium, (cyclopentadienyl)(tri-tert-butylphosphineimine)(2,3-diphenylbutadiene)titanium, (cyclopentadienyl)(tri-n-pentylphosphineimine)(butadiene)titanium, (cyclopentadienyl)(tri-n-pentylphosphineimine)(1,3-pentadiene)titanium, (cyclopentadienyl)(tri-n-pentylphosphineimine)(isoprene)titanium, (cyclopentadienyl)(tri-n-pentylphosphineimine)(1,3-hexadiene)titanium, (cyclopentadienyl)(tri-n-pentylphosphineimine)(2,4-hexadiene)titanium, (cyclopentadienyl)(tri-n-pentylphosphineimine)(2,3-dimethylbutadiene)titanium, (cyclopentadienyl)(tri-n-pentylphosphineimine)(1,3-heptadiene)titanium, (cyclopentadienyl)(tri-n-pentylphosphineimine)(2,4-heptadiene)titanium, (cyclopentadienyl)(tri-n-pentylphosphineimine)(2,3-dimethyl-1,3-pentadiene)titanium, (cyclopentadienyl)(tri-n-pentylphosphineimine)(1,3-octadiene)titanium, (cyclopentadienyl)(tri-n-pentylphosphineimine)(2,4-octadiene)titanium, (cyclopentadienyl)(tri-n-pentylphosphineimine)(3,5-octadiene)titanium, (cyclopentadienyl)(tri-n-pentylphosphineimine)(3,4-dimethyl-2,4-hexadiene)titanium, (cyclopentadienyl)(tri-n-pentylphosphineimine)(5,5-dimethyl-1,3-hexadiene)titanium, (cyclopentadienyl)(tri-n-pentylphosphineimine)(2,7-dimethyl-3,5-octadiene)titanium, (cyclopentadienyl)(tri-n-pentylphosphineimine)(4,5-dimethyl-3,5-octadiene)titanium, (cyclopentadienyl)(tri-n-pentylphosphineimine)(2,2,7,7-tetramethyl-3,5-octadiene)titanium, (cyclopentadienyl)(tri-n-pentylphosphineimine)(2,4,5,7-tetramethyl-3,5-octadiene)titanium, (cyclopentadienyl)(tri-n-pentylphosphineimine)(1-phenylbutadiene)titanium, (cyclopentadienyl)(tri-n-pentylphosphineimine)(2-phenylbutadiene)titanium, (cyclopentadienyl)(tri-n-pentylphosphineimine)(1,4-diphenylbutadiene)titanium, (cyclopentadienyl)(tri-n-pentylphosphineimine)(2,3-diphenylbutadiene)titanium, (cyclopentadienyl)(tri-sec-pentylphosphineimine)(butadiene)titanium, (cyclopentadienyl)(tri-sec-pentylphosphineimine)(1,3-pentadiene)titanium, (cyclopentadienyl)(tri-sec-pentylphosphineimine)(isoprene)titanium, (cyclopentadienyl)(tri-sec-pentylphosphineimine)(1,3-hexadiene)titanium, (cyclopentadienyl)(tri-sec-pentylphosphineimine)(2,4-hexadiene)titanium, (cyclopentadienyl)(tri-sec-pentylphosphineimine)(2,3-dimethylbutadiene)titanium, (cyclopentadienyl)(tri-sec-pentylphosphineimine)(1,3-heptadiene)titanium, (cyclopentadienyl)(tri-sec-pentylphosphineimine)(2,4-heptadiene)titanium, (cyclopentadienyl)(tri-sec-pentylphosphineimine)(2,3-dimethyl-1,3-pentadiene)titanium, (cyclopentadienyl)(tri-sec-pentylphosphineimine)(1,3-octadiene)titanium, (cyclopentadienyl)(tri-sec-pentylphosphineimine)(2,4-octadiene)titanium, (cyclopentadienyl)(tri-sec-pentylphosphineimine)(3,5-octadiene)titanium, (cyclopentadienyl)(tri-sec-pentylphosphineimine)(3,4-dimethyl-2,4-hexadiene)titanium, (cyclopentadienyl)(tri-sec-pentylphosphineimine)(5,5-dimethyl-1,3-hexadiene)titanium, (cyclopentadienyl)(tri-sec-pentylphosphineimine)(2,7-dimethyl-3,5-octadiene)titanium, (cyclopentadienyl)(tri-sec-pentylphosphineimine)(4,5-dimethyl-3,5-octadiene)titanium, (cyclopentadienyl)(tri-sec-pentylphosphineimine)(2,2,7,7-tetramethyl-3,5-octadiene)titanium, (cyclopentadienyl)(tri-sec-pentylphosphineimine)(2,4,5,7-tetramethyl-3,5-octadiene)titanium, (cyclopentadienyl)(tri-sec-pentylphosphineimine)(1-phenylbutadiene)titanium, (cyclopentadienyl)(tri-sec-pentylphosphineimine)(2-phenylbutadiene)titanium, (cyclopentadienyl)(tri-sec-pentylphosphineimine)(1,4-diphenylbutadiene)titanium, (cyclopentadienyl)(tri-sec-pentylphosphineimine)(2,3-diphenylbutadiene)titanium, (cyclopentadienyl)(triisopentylphosphineimine)(butadiene)titanium, (cyclopentadienyl)(triisopentylphosphineimine)(1,3-pentadiene)titanium, (cyclopentadienyl)(triisopentylphosphineimine)(isoprene) titanium, (cyclopentadienyl)(triisopentylphosphineimine)(1,3-hexadiene)titanium, (cyclopentadienyl)(triisopentylphosphineimine)(2,4-hexadiene)titanium, (cyclopentadienyl)(triisopentylphosphineimine)(2,3-dimethylbutadiene)titanium, (cyclopentadienyl)(triisopentylphosphineimine)(1,3-heptadiene)titanium, (cyclopentadienyl)(triisopentylphosphineimine)(2,4-heptadiene)titanium, (cyclopentadienyl)(triisopentylphosphineimine)(2,3-dimethyl-1,3-pentadiene)titanium, (cyclopentadienyl)(triisopentylphosphineimine)(1,3-octadiene)titanium, (cyclopentadienyl)(triisopentylphosphineimine)(2,4-octadiene)titanium, (cyclopentadienyl)(triisopentylphosphineimine)(3,5-octadiene)titanium, (cyclopentadienyl)(triisopentylphosphineimine)(3,4-dimethyl-2,4-hexadiene)titanium, (cyclopentadienyl)(triisopentylphosphineimine)(5,5-dimethyl-1,3-hexadiene)titanium, (cyclopentadienyl)(triisopentylphosphineimine)(2,7-dimethyl-3,5-octadiene)titanium, (cyclopentadienyl)(triisopentylphosphineimine)(4,5-dimethyl-3,5-octadiene)titanium, (cyclopentadienyl)(triisopentylphosphineimine)(2,2,7,7-tetramethyl-3,5-octadiene)titanium, (cyclopentadienyl)(triisopentylphosphineimine)(2,4,5,7-tetramethyl-3,5-octadiene)titanium, (cyclopentadienyl)(triisopentylphosphineimine)(1-phenylbutadiene)titanium, (cyclopentadienyl)(triisopentylphosphineimine)(2- phenylbutadiene)titanium, (cyclopentadienyl)(triisopentylphosphineimine)(1,4-diphenylbutadiene)titanium, (cyclopentadienyl)(triisopentylphosphineimine)(2,3-diphenylbutadiene)titanium, (cyclopentadienyl)(tri-tert-pentylphosphineimine)(butadiene)titanium, (cyclopentadienyl)(tri-tert-pentylphosphineimine)(pentadiene)titanium, (cyclopentadienyl)(tri-tert-pentylphosphineimine)(isoprene)titanium, (cyclopentadienyl)(tri-tert-pentylphosphineimine)(1,3-hexadiene)titanium, (cyclopentadienyl)(tri-tert-pentylphosphineimine)(2,4-hexadiene)titanium, (cyclopentadienyl)(tri-tert-pentylphosphineimine)(2,3-dimethylbutadiene)titanium, (cyclopentadienyl)(tri-tert-pentylphosphineimine)(1,3-heptadiene)titanium, (cyclopentadienyl)(tri-tert-pentylphosphineimine)(2,4-heptadiene)titanium, (cyclopentadienyl)(tri-tert-pentylphosphineimine)(2,3-dimethyl-1,3-pentadiene)titanium, (cyclopentadienyl)(tri-tert-pentylphosphineimine)(1,3-octadiene)titanium, (cyclopentadienyl)(tri-tert-pentylphosphineimine)(2,4-octadiene)titanium, (cyclopentadienyl)(tri-tert-pentylphosphineimine)(3,5-octadiene)titanium, (cyclopentadienyl)(tri-tert-pentylphosphineimine)(3,4-dimethyl-2,4-hexadiene)titanium, (cyclopentadienyl)(tri-tert-pentylphosphineimine)(5,5-dimethyl-1,3-hexadiene)titanium, (cyclopentadienyl)(tri-tert-pentylphosphineimine)(2,7-dimethyl-3,5-octadiene)titanium, (cyclopentadienyl)(tri-tert-pentylphosphineimine)(4,5-dimethyl-3,5-octadiene)titanium, (cyclopentadienyl)(tri-tert-pentylphosphineimine)(2,2,7,7-tetramethyl-3,5-octadiene)titanium, (cyclopentadienyl)(tri-tert-pentylphosphineimine)(2,4,5,7-tetramethyl-3,5-octadiene)titanium, (cyclopentadienyl)(tri-tert-pentylphosphineimine)(1-phenylbutadiene)titanium, (cyclopentadienyl)(tri-tert-pentylphosphineimine)(2-phenylbutadiene)titanium, (cyclopentadienyl)(tri-tert-pentylphosphineimine)(1,4-diphenylbutadiene)titanium, (cyclopentadienyl)(tri-tert-pentylphosphineimine)(2,3-diphenylbutadiene)titanium, (cyclopentadienyl)(trineopentylphosphineimine)(butadiene)titanium, (cyclopentadienyl)(trineopentylphosphineimine)(pentadiene)titanium, (cyclopentadienyl)(trineopentylphosphineimine)(isoprene)titanium, (cyclopentadienyl)(trineopentylphosphineimine)(1,3-hexadiene)titanium, (cyclopentadienyl)(trineopentylphosphineimine)(2,4-hexadiene)titanium, (cyclopentadienyl)(trineopentylphosphineimine)(2,3-dimethylbutadiene)titanium, (cyclopentadienyl)(trineopentylphosphineimine)(1,3-heptadiene)titanium, (cyclopentadienyl)(trineopentylphosphineimine)(2,4-heptadiene)titanium, (cyclopentadienyl)(trineopentylphosphineimine)(2,3-dimethyl-1,3-pentadiene)titanium, (cyclopentadienyl)(trineopentylphosphineimine)(1,3-octadiene)titanium, (cyclopentadienyl)(trineopentylphosphineimine)(2,4-octadiene)titanium, (cyclopentadienyl)(trineopentylphosphineimine)(3,5-octadiene)titanium, (cyclopentadienyl)(trineopentylphosphineimine)(3,4-dimethyl-2,4-hexadiene)titanium, (cyclopentadienyl)(trineopentylphosphineimine)(5,5-dimethyl-1,3-hexadiene)titanium, (cyclopentadienyl)(trineopentylphosphineimine)(2,7-dimethyl-3,5-octadiene)titanium, (cyclopentadienyl)(trineopentylphosphineimine)(4,5-dimethyl-3,5-octadiene)titanium, (cyclopentadienyl)(trineopentylphosphineimine)(2,2,7,7-tetramethyl-3,5-octadiene)titanium, (cyclopentadienyl)(trineopentylphosphineimine)(2,4,5,7-tetramethyl-3,5-octadiene)titanium, (cyclopentadienyl)(trineopentylphosphineimine)(1-phenylbutadiene)titanium, (cyclopentadienyl)(trineopentylphosphineimine)(2-phenylbutadiene)titanium, (cyclopentadienyl)(trineopentylphosphineimine)(1,4-diphenylbutadiene)titanium, (cyclopentadienyl)(trineopentylphosphineimine)(2,3-diphenylbutadiene)titanium, (cyclopentadienyl)(tricyclopentylphosphineimine)(butadiene)titanium, (cyclopentadienyl)(tricyclopentylphosphineimine)(1,3-pentadiene)titanium, (cyclopentadienyl)(tricyclopentylphosphineimine)(isoprene)titanium, (cyclopentadienyl)(tricyclopentylphosphineimine)(1,3-hexadiene)titanium, (cyclopentadienyl)(tricyclopentylphosphineimine)(2,4-hexadiene)titanium, (cyclopentadienyl)(tricyclopentylphosphineimine)(2,3-dimethylbutadiene)titanium, (cyclopentadienyl)(tricyclopentylphosphineimine)(1,3-heptadiene)titanium, (cyclopentadienyl)(tricyclopentylphosphineimine)(2,4-heptadiene)titanium, (cyclopentadienyl)(tricyclopentylphosphineimine)(2,3-dimethyl-1,3-pentadiene)titanium, (cyclopentadienyl)(tricyclopentylphosphineimine)(1,3-octadiene)titanium, (cyclopentadienyl)(tricyclopentylphosphineimine)(2,4-octadiene)titanium, (cyclopentadienyl)(tricyclopentylphosphineimine)(3,5-octadiene)titanium, (cyclopentadienyl)(tricyclopentylphosphineimine)(3,4-dimethyl-2,4-hexadiene)titanium, (cyclopentadienyl)(tricyclopentylphosphineimine)(5,5-dimethyl-1,3-hexadiene)titanium, (cyclopentadienyl)(tricyclopentylphosphineimine)(2,7-dimethyl-3,5-octadiene)titanium, (cyclopentadienyl)(tricyclopentylphosphineimine)(4,5-dimethyl-3,5-octadiene)titanium, (cyclopentadienyl)(tricyclopentylphosphineimine)(2,2,7,7-tetramethyl-3,5-octadiene)titanium, (cyclopentadienyl)(tricyclopentylphosphineimine)(2,4,5,7-tetramethyl-3,5-octadiene)titanium, (cyclopentadienyl)(tricyclopentylphosphineimine)(1-phenylbutadiene)titanium, (cyclopentadienyl)(tricyclopentylphosphineimine)(2-phenylbutadiene)titanium, (cyclopentadienyl)(tricyclopentylphosphineimine)(1,4-diphenylbutadiene)titanium, (cyclopentadienyl)(tricyclopentylphosphineimine)(2,3-diphenylbutadiene)titanium, (cyclopentadienyl)(tri-n-hexylphosphineimine)(butadiene)titanium, (cyclopentadienyl)(tri-n-hexylphosphineimine)(1,3-pentadiene)titanium, (cyclopentadienyl)(tri-n-hexylphosphineimine)(isoprene)titanium, (cyclopentadienyl)(tri-n-hexylphosphineimine)(1,3-hexadiene)titanium, (cyclopentadienyl)(tri-n-hexylphosphineimine)(2,4-hexadiene)titanium, (cyclopentadienyl)(tri-n-hexylphosphineimine)(2,3-dimethylbutadiene)titanium, (cyclopentadienyl)(tri-n-hexylphosphineimine)(1,3-heptadiene)titanium, (cyclopentadienyl)(tri-n-hexylphosphineimine)(2,4-heptadiene)titanium, (cyclopentadienyl)(tri-n-hexylphosphineimine)(2,3-dimethyl-1,3-pentadiene)titanium, (cyclopentadienyl)(tri-n-hexylphosphineimine)(1,3-octadiene)titanium, (cyclopentadienyl)(tri-n-hexylphosphineimine)(2,4-octadiene)titanium, (cyclopentadienyl)(tri-n-hexylphosphineimine)(3,5-octadiene)titanium, (cyclopentadienyl)(tri-n-hexylphosphineimine)(3,4-dimethyl-2,4-hexadiene)titanium, (cyclopentadienyl)(tri-n-hexylphosphineimine)(5,5-dimethyl-1,3-hexadiene)titanium, (cyclopentadienyl)(tri-n-hexylphosphineimine)(2,7-dimethyl-3,5-octadiene)titanium, (cyclopentadienyl)(tri-n-hexylphosphineimine)(4,5-dimethyl-3,5-octadiene)titanium, (cyclopentadienyl)(tri-n-hexylphosphineimine)(2,2,7,7-tetramethyl-3,5-octadiene)titanium, (cyclopentadienyl)(tri-n-hexylphosphineimine)(2,4,5,7-tetramethyl-3,5-octadiene)titanium, (cyclopentadienyl)(tri-n-hexylphosphineimine)(1-phenylbutadiene)titanium, (cyclopentadienyl)(tri-n-hexylphosphineimine)(2-phenylbutadiene)titanium, (cyclopentadienyl)(tri-n-hexylphosphineimine)(1,4-diphenylbutadiene)titanium, (cyclopentadienyl)(tri-n-hexylphosphineimine)(2,3-diphenylbutadiene)titanium, (cyclopentadienyl)(tri-sec-hexylphosphineimine)(butadiene)titanium, (cyclopentadienyl)(tri-sec-hexylphosphineimine)(1,3-pentadiene)titanium, (cyclopentadienyl)(tri-sec-hexylphosphineimine)(isoprene)titanium, (cyclopentadienyl)(tri-sec-hexylphosphineimine)(1,3-hexadiene)titanium, (cyclopentadienyl)(tri-sec-hexylphosphineimine)(2,4-hexadiene)titanium, (cyclopentadienyl)(tri-sec-hexylphosphineimine)(2,3-dimethylbutadiene)titanium, (cyclopentadienyl)(tri-sec-hexylphosphineimine)(1,3-heptadiene)titanium, (cyclopentadienyl)(tri-sec-hexylphosphineimine)(2,4-heptadiene)titanium, (cyclopentadienyl)(tri-sec-hexylphosphineimine)(2,3-dimethyl-1,3-pentadiene)titanium, (cyclopentadienyl)(tri-sec-hexylphosphineimine)(1,3-octadiene)titanium, (cyclopentadienyl)(tri-sec-hexylphosphineimine)(2,4-octadiene)titanium, (cyclopentadienyl)(tri-sec-hexylphosphineimine)(3,5-octadiene)titanium, (cyclopentadienyl)(tri-sec-hexylphosphineimine)(3,4-dimethyl-2,4-hexadiene)titanium, (cyclopentadienyl)(tri-sec-hexylphosphineimine)(5,5-dimethyl-1,3-hexadiene)titanium, (cyclopentadienyl)(tri-sec-hexylphosphineimine)(2,7-dimethyl-3,5-octadiene)titanium, (cyclopentadienyl)(tri-sec-hexylphosphineimine)(4,5-dimethyl-3,5-octadiene)titanium, (cyclopentadienyl)(tri-sec-hexylphosphineimine)(2,2,7,7-tetramethyl-3,5-octadiene)titanium, (cyclopentadienyl)(tri-sec-hexylphosphineimine)(2,4,5,7-tetramethyl-3,5-octadiene)titanium, (cyclopentadienyl)(tri-sec-hexylphosphineimine)(1-phenylbutadiene)titanium, (cyclopentadienyl)(tri-sec-hexylphosphineimine)(2-phenylbutadiene)titanium, (cyclopentadienyl)(tri-sec-hexylphosphineimine)(1,4-diphenylbutadiene)titanium, (cyclopentadienyl)(tri-sec-hexylphosphineimine)(2,3-diphenylbutadiene)titanium, (cyclopentadienyl)(triisohexylphosphineimine)(butadiene)titanium, (cyclopentadienyl)(triisohexylphosphineimine)(1,3-pentadiene)titanium, (cyclopentadienyl)(triisohexylphosphineimine)(isoprene)titanium, (cyclopentadienyl)(triisohexylphosphineimine)(1,3-hexadiene)titanium, (cyclopentadienyl)(triisohexylphosphineimine)(2,4-hexadiene)titanium, (cyclopentadienyl)(triisohexylphosphineimine)(2,3-dimethylbutadiene)titanium, (cyclopentadienyl)(triisohexylphosphineimine)(1,3-heptadiene)titanium, (cyclopentadienyl)(triisohexylphosphineimine)(2,4-heptadiene)titanium, (cyclopentadienyl)(triisohexylphosphineimine)(2,3-dimethyl-1,3-pentadiene)titanium, (cyclopentadienyl)(triisohexylphosphineimine)(1,3-octadiene)titanium, (cyclopentadienyl)(triisohexylphosphineimine)(2,4-octadiene)titanium, (cyclopentadienyl)(triisohexylphosphineimine)(3,5-octadiene)titanium, (cyclopentadienyl)(triisohexylphosphineimine)(3,4-dimethyl-2,4-hexadiene)titanium, (cyclopentadienyl)(triisohexylphosphineimine)(5,5-dimethyl-1,3-hexadiene)titanium, (cyclopentadienyl)(triisohexylphosphineimine)(2,7-dimethyl-3,5-octadiene)titanium, (cyclopentadienyl)(triisohexylphosphineimine)(4,5-dimethyl-3,5-octadiene)titanium, (cyclopentadienyl)(triisohexylphosphineimine)(2,2,7,7-tetramethyl-3,5-octadiene)titanium, (cyclopentadienyl)(triisohexylphosphineimine)(2,4,5,7-tetramethyl-3,5-octadiene)titanium, (cyclopentadienyl)(triisohexylphosphineimine)(1-phenylbutadiene)titanium, (cyclopentadienyl)(triisohexylphosphineimine)(2-phenylbutadiene)titanium, (cyclopentadienyl)(triisohexylphosphineimine)(1,4-diphenylbutadiene)titanium, (cyclopentadienyl)(triisohexylphosphineimine)(2,3-diphenylbutadiene)titanium, (cyclopentadienyl)(tri-tert-hexylphosphineimine)(butadiene)titanium, (cyclopentadienyl)(tri-tert-hexylphosphineimine)(1,3-pentadiene)titanium, (cyclopentadienyl)(tri-tert-hexylphosphineimine)(isoprene)titanium, (cyclopentadienyl)(tri-tert-hexylphosphineimine)(1,3-hexadiene)titanium, (cyclopentadienyl)(tri-tert-hexylphosphineimine)(2,4-hexadiene)titanium, (cyclopentadienyl)(tri-tert-hexylphosphineimine)(2,3-dimethylbutadiene)titanium, (cyclopentadienyl)(tri-tert-hexylphosphineimine)(1,3-heptadiene)titanium, (cyclopentadienyl)(tri-tert-hexylphosphineimine)(2,4-heptadiene)titanium, (cyclopentadienyl)(tri-tert-hexylphosphineimine)(2,3-dimethyl-1,3-pentadiene)titanium, (cyclopentadienyl)(tri-tert-hexylphosphineimine)(1,3-octadiene)titanium, (cyclopentadienyl)(tri-tert-hexylphosphineimine)(2,4-octadiene)titanium, (cyclopentadienyl)(tri-tert-hexylphosphineimine)(3,5-octadiene)titanium, (cyclopentadienyl)(tri-tert-hexylphosphineimine)(3,4-dimethyl-2,4-hexadiene)titanium, (cyclopentadienyl)(tri-tert-hexylphosphineimine)(5,5-dimethyl-1.3-hexadiene)titanium, (cyclopentadienyl)(tri-tert-hexylphosphineimine)(2,7-dimethyl-3,5-octadiene)titanium, (cyclopentadienyl)(tri-tert-hexylphosphineimine)(4,5-dimethyl-3,5-octadiene)titanium, (cyclopentadienyl)(tri-tert-hexylphosphineimine)(2,2,7,7-tetramethyl-3,5-octadiene)titanium, (cyclopentadienyl)(tri-tert-hexylphosphineimine)(2,4,5,7-tetramethyl-3,5-octadiene)titanium, (cyclopentadienyl)(tri-tert-hexylphosphineimine)(1-phenylbutadiene)titanium, (cyclopentadienyl)(tri-tert-hexylphosphineimine)(2-phenylbutadiene)titanium, (cyclopentadienyl)(tri-tert-hexylphosphineimine)(1,4-diphenylbutadiene)titanium, (cyclopentadienyl)(tri-tert-hexylphosphineimine)(2,3-diphenylbutadiene)titanium, (cyclopentadienyl)(trineohexylphosphineimine)(butadiene)titanium, (cyclopentadienyl)(trineohexylphosphineimine)(1,3-pentadiene)titanium, (cyclopentadienyl)(trineohexylphosphineimine)(isoprene)titanium, (cyclopentadienyl)(trineohexylphosphineimine)(1,3-hexadiene)titanium, (cyclopentadienyl)(trineohexylphosphineimine)(2,4-hexadiene)titanium, (cyclopentadienyl)(trineohexylphosphineimine)(2,3-dimethylbutadiene)titanium, (cyclopentadienyl)(trineohexylphosphineimine)(1,3-heptadiene)titanium, (cyclopentadienyl)(trineohexylphosphineimine)(2,4-heptadiene)titanium, (cyclopentadienyl)(trineohexylphosphineimine)(2,3-dimethyl-1,3-pentadiene)titanium, (cyclopentadienyl)(trineohexylphosphineimine)(1,3-octadiene)titanium, (cyclopentadienyl)(trineohexylphosphineimine)(2,4-octadiene)titanium, (cyclopentadienyl)(trineohexylphosphineimine)(3,5-octadiene)titanium, (cyclopentadienyl)(trineohexylphosphineimine)(3,4-dimethyl-2,4-hexadiene)titanium, (cyclopentadienyl)(trineohexylphosphineimine)(5,5-dimethyl-1,3-hexadiene)titanium, (cyclopentadienyl)(trineohexylphosphineimine)(2,7-dimethyl-3,5-octadiene)titanium, (cyclopentadienyl)(trineohexylphosphineimine)(4,5-dimethyl-3,5-octadiene)titanium, (cyclopentadienyl)(trineohexylphosphineimine)(2,2,7,7-tetramethyl-3,5-octadiene)titanium, (cyclopentadienyl)(trineohexylphosphineimine)(2,4,5,7-tetramethyl-3,5-octadiene)titanium, (cyclopentadienyl)

(trineohexylphosphineimine)(1-phenylbutadiene)titanium, (cyclopentadienyl)(trineohexylphosphineimine)(2-phenylbutadiene)titanium, (cyclopentadienyl)(trineohexylphosphineimine)(1,4-diphenylbutadiene)titanium, (cyclopentadienyl)(trineohexylphosphineimine)(2,3-diphenylbutadiene)titanium, (cyclopentadienyl)(tricyclohexylphosphineimine)(butadiene)titanium, (cyclopentadienyl)(tricyclohexylphosphineimine)(pentadiene)titanium, (cyclopentadienyl)(tricyclohexylphosphineimine)(isoprene)titanium, (cyclopentadienyl)(tricyclohexylphosphineimine)(1,3-hexadiene)titanium, (cyclopentadienyl)(tricyclohexylphosphineimine)(2,4-hexadiene)titanium, (cyclopentadienyl)(tricyclohexylphosphineimine)(2,3-dimethylbutadiene)titanium, (cyclopentadienyl)(tricyclohexylphosphineimine)(1,3-heptadiene)titanium, (cyclopentadienyl)(tricyclohexylphosphineimine)(2,4-heptadiene)titanium, (cyclopentadienyl)(tricyclohexylphosphineimine)(2,3-dimethyl-1,3-pentadiene)titanium, (cyclopentadienyl)(tricyclohexylphosphineimine)(1,3-octadiene)titanium, (cyclopentadienyl)(tricyclohexylphosphineimine)(2,4-octadiene)titanium, (cyclopentadienyl)(tricyclohexylphosphineimine)(3,5-octadiene)titanium, (cyclopentadienyl)(tricyclohexylphosphineimine)(3,4-dimethyl-2,4-hexadiene)titanium, (cyclopentadienyl)(tricyclohexylphosphineimine)(5,5-dimethyl-1,3-hexadiene)titanium, (cyclopentadienyl)(tricyclohexylphosphineimine)(2,7-dimethyl-3,5-octadiene)titanium, (cyclopentadienyl)(tricyclohexylphosphineimine)(4,5-dimethyl-3,5-octadiene)titanium, (cyclopentadienyl)(tricyclohexylphosphineimine)(2,2,7,7-tetramethyl-3,5-octadiene)titanium, (cyclopentadienyl)(tricyclohexylphosphineimine)(2,4,5,7-tetramethyl-3,5-octadiene)titanium, (cyclopentadienyl)(tricyclohexylphosphineimine)(1-phenylbutadiene)titanium, (cyclopentadienyl)(tricyclohexylphosphineimine)(2-phenylbutadiene)titanium, (cyclopentadienyl)(tricyclohexylphosphineimine)(1,4-diphenylbutadiene)titanium, (cyclopentadienyl)(tricyclohexylphosphineimine)(2,3-diphenylbutadiene)titanium, (cyclopentadienyl)(triphenylphosphineimine)(butadiene)titanium, (cyclopentadienyl)(triphenylphosphineimine)(1,3-pentadiene)titanium, (cyclopentadienyl)(triphenylphosphineimine)(isoprene)titanium, (cyclopentadienyl)(triphenylphosphineimine)(1,3-hexadiene)titanium, (cyclopentadienyl)(triphenylphosphineimine)(2,4-hexadiene)titanium, (cyclopentadienyl)(triphenylphosphineimine)(2,3-dimethylbutadiene)titanium, (cyclopentadienyl)(triphenylphosphineimine)(1,3-heptadiene)titanium, (cyclopentadienyl)(triphenylphosphineimine)(2,4-heptadiene)titanium, (cyclopentadienyl)(triphenylphosphineimine)(2,3-dimethyl-1,3-pentadiene)titanium, (cyclopentadienyl)(triphenylphosphineimine)(1,3-octadiene)titanium, (cyclopentadienyl)(triphenylphosphineimine)(2,4-octadiene)titanium, (cyclopentadienyl)(triphenylphosphineimine)(3,5-octadiene)titanium, (cyclopentadienyl)(triphenylphosphineimine)(3,4-dimethyl-2,4-hexadiene)titanium, (cyclopentadienyl)(triphenylphosphineimine)(5,5-dimethyl-1,3-hexadiene)titanium, (cyclopentadienyl)(triphenylphosphineimine)(2,7-dimethyl-3,5-octadiene)titanium, (cyclopentadienyl)(triphenylphosphineimine)(4,5-dimethyl-3,5-octadiene)titanium, (cyclopentadienyl)(triphenylphosphineimine)(2,2,7,7-tetramethyl-3,5-octadiene)titanium, (cyclopentadienyl)(triphenylphosphineimine)(2,4,5,7-tetramethyl-3,5-octadiene)titanium, (cyclopentadienyl)(triphenylphosphineimine)(1-phenylbutadiene)titanium, (cyclopentadienyl)(triphenylphosphineimine)(2-phenylbutadiene)titanium, (cyclopentadienyl)(triphenylphosphineimine)(1,4-diphenylbutadiene)titanium, (cyclopentadienyl)(triphenylphosphineimine)(2,3-diphenylbutadiene)titanium, (cyclopentadienyl)(tritolylphosphineimine)(butadiene)titanium, (cyclopentadienyl)(tritolylphosphineimine)(1,3-pentadiene)titanium, (cyclopentadienyl)(tritolylphosphineimine)(isoprene)titanium, (cyclopentadienyl)(tritolylphosphineimine)(1,3-hexadiene)titanium, (cyclopentadienyl)(tritolylphosphineimine)(2,4-hexadiene)titanium, (cyclopentadienyl)(tritolylphosphineimine)(2,3-dimethylbutadiene)titanium, (cyclopentadienyl)(tritolylphosphineimine)(1,3-heptadiene)titanium, (cyclopentadienyl)(tritolylphosphineimine)(2,4-heptadiene)titanium, (cyclopentadienyl)(tritolylphosphineimine)(2,3-dimethyl-1,3-pentadiene)titanium, (cyclopentadienyl)(tritolylphosphineimine)(1,3-octadiene)titanium, (cyclopentadienyl)(tritolylphosphineimine)(2,4-octadiene)titanium, (cyclopentadienyl)(tritolylphosphineimine)(3,5-octadiene)titanium, (cyclopentadienyl)(tritolylphosphineimine)(3,4-dimethyl-2,4-hexadiene)titanium, (cyclopentadienyl)(tritolylphosphineimine)(5,5-dimethyl-1,3-hexadiene)titanium, (cyclopentadienyl)(tritolylphosphineimine)(2,7-dimethyl-3,5-octadiene)titanium, (cyclopentadienyl)(tritolylphosphineimine)(4,5-dimethyl-3,5-octadiene)titanium, (cyclopentadienyl)(tritolylphosphineimine)(2,2,7,7-tetramethyl-3,5-octadiene)titanium, (cyclopentadienyl)(tritolylphosphineimine)(2,4,5,7-tetramethyl-3,5-octadiene)titanium, (cyclopentadienyl)(tritolylphosphineimine)(1-phenylbutadiene)titanium, (cyclopentadienyl)(tritolylphosphineimine)(2-phenylbutadiene)titanium, (cyclopentadienyl)(tritolylphosphineimine)(1,4-diphenylbutadiene)titanium, (cyclopentadienyl)(tritolylphosphineimine)(2,3-diphenylbutadiene)titanium, (cyclopentadienyl) [tris(trimethylsilyl)phosphineimine](butadiene)titanium, (cyclopentadienyl)[tris(trimethylsilyl)phosphineimine](1,3-pentadiene)titanium, (cyclopentadienyl)[tris(trimethylsilyl)phosphineimine](isoprene)titanium, (cyclopentadienyl)[tris(trimethylsilyl)phosphineimine](1,3-hexadiene)titanium, (cyclopentadienyl)[tris(trimethylsilyl)phosphineimine](2,4-hexadiene)titanium, (cyclopentadienyl)[tris(trimethylsilyl)phosphineimine](2,3-dimethylbutadiene)titanium, (cyclopentadienyl)[tris(trimethylsilyl)phosphineimine](1,3-heptadiene)titanium, (cyclopentadienyl)[tris(trimethylsilyl)phosphineimine](2,4-heptadiene)titanium, (cyclopentadienyl)[tris(trimethylsilyl)phosphineimine](2,3-dimethyl-1,3-pentadiene)titanium, (cyclopentadienyl)[tris(trimethylsilyl)phosphineimine](1,3-octadiene)titanium, (cyclopentadienyl)[tris(trimethylsilyl)phosphineimine](2,4-octadiene)titanium, (cyclopentadienyl)[tris(trimethylsilyl)phosphineimine](3,5-octadiene)titanium, (cyclopentadienyl)[tris(trimethylsilyl)phosphineimine](3,4-dimethyl-2,4-hexadiene)titanium, (cyclopentadienyl)[tris(trimethylsilyl)phosphineimine](5,5-dimethyl-1,3-hexadiene)titanium, (cyclopentadienyl)[tris(trimethylsilyl)phosphineimine](2,7-dimethyl-3,5-octadiene)titanium, (cyclopentadienyl)[tris(trimethylsilyl)phosphineimine](4,5-dimethyl-3,5-octadiene)titanium, (cyclopentadienyl)[tris(trimethylsilyl)phosphineimine](2,2,7,7-tetramethyl-3,5-octadiene)titanium, (cyclopentadienyl)[tris(trimethylsilyl)phosphineimine](2,4,5,7-tetramethyl-3,5-octadiene)titanium, (cyclopentadienyl)[tris(trimethylsilyl)

phosphineimine](1-phenylbutadiene)titanium, (cyclopentadienyl)[tris(trimethylsilyl)phosphineimine](2-phenylbutadiene)titanium, (cyclopentadienyl)[tris(trimethylsilyl)phosphineimine](1,4-diphenylbutadiene)titanium, (cyclopentadienyl)[tris(trimethylsilyl)phosphineimine](2,3-diphenylbutadiene)titanium, (cyclopentadienyl)[tris(butyldimethylsilyl)phosphineimine](butadiene)titanium, (cyclopentadienyl)[tris(butyldimethylsilyl)phosphineimine](1,3-pentadiene)titanium, (cyclopentadienyl)[tris(butyldimethylsilyl)phosphineimine](isoprene)titanium, (cyclopentadienyl)[tris(butyldimethylsilyl)phosphineimine](1,3-hexadiene)titanium, (cyclopentadienyl)[tris(butyldimethylsilyl)phosphineimine](2,4-hexadiene)titanium, (cyclopentadienyl)[tris(butyldimethylsilyl)phosphineimine](2,3-dimethylbutadiene)titanium, (cyclopentadienyl)[tris(butyldimethylsilyl)phosphineimine](1,3-heptadiene)titanium, (cyclopentadienyl)[tris(butyldimethylsilyl)phosphineimine](2,4-heptadiene)titanium, (cyclopentadienyl)[tris(butyldimethylsilyl)phosphineimine](2,3-dimethyl-1,3-pentadiene)titanium, (cyclopentadienyl)[tris(butyldimethylsilyl)phosphineimine](1,3-octadiene)titanium, (cyclopentadienyl)[tris(butyldimethylsilyl)phosphineimine](2,4-octadiene)titanium, (cyclopentadienyl)[tris(butyldimethylsilyl)phosphineimine](3,5-octadiene)titanium, (cyclopentadienyl)[tris(butyldimethylsilyl)phosphineimine](3,4-dimethyl-2,4-hexadiene)titanium, (cyclopentadienyl)[tris(butyldimethylsilyl)phosphineimine](5,5-dimethyl-1,3-hexadiene)titanium, (cyclopentadienyl)[tris(butyldimethylsilyl)phosphineimine](2,7-dimethyl-3,5-octadiene)titanium, (cyclopentadienyl)[tris(butyldimethylsilyl)phosphineimine](4,5-dimethyl-3,5-octadiene)titanium, (cyclopentadienyl)[tris(butyldimethylsilyl)phosphineimine](2,2,7,7-tetramethyl-3,5-octadiene)titanium, (cyclopentadienyl)[tris(butyldimethylsilyl)phosphineimine](2,4,5,7-tetramethyl-3,5-octadiene)titanium, (cyclopentadienyl)[tris(butyldimethylsilyl)phosphineimine](1-phenylbutadiene)titanium, (cyclopentadienyl)[tris(butyldimethylsilyl)phosphineimine](2-phenylbutadiene)titanium, (cyclopentadienyl)[tris(butyldimethylsilyl)phosphineimine](1,4-diphenylbutadiene)titanium, (cyclopentadienyl)[tris(butyldimethylsilyl)phosphineimine](2,3-diphenylbutadiene)titanium and the like, and transition metal compounds such as compounds obtained by replacing titanium on these compounds with zirconium or hafnium and compounds obtained by replacing cyclopentadienyl on these compounds with dimethylcyclopentadienyl, trimethylcyclopentadienyl, tetramethylcyclopentadienyl, n-butylcyclopentadienyl, tert-butyldimethylsilylcyclopentadienyl, indenyl, tetrahydroindenyl, fluorenyl or octahydrofluorenyl.

The transition metal compound (A) of the present invention is useful as an addition polymerization catalyst component which can manifest high polymerization activity. The addition polymerization catalyst of the present invention is an addition polymerization catalyst which is prepared by using the above-described transition metal compound (A) and preferably prepared by contacting the above-described transition metal compound (A) with a co-catalyst for activation.

As the co-catalyst for activation, an organoaluminum compound (B) and/or the following (C) is preferably used.
(C) Any boron compound of the following (C1) to (C3)
(C1) A boron compound represented by the general formula $BQ^1Q^2Q^3$ (C2) A boron compound represented by the general formula $G^+(BQ^1Q^2Q^3Q^4)^-$
(C3) A boron compound represented by the general formula $(L—H)^+(BQ^1Q^2Q^3Q^4)^-$
(wherein, B is a boron atom in the trivalent valence state, $Q^1$ to $Q^4$ are a halogen atom, hydrocarbon group, halogenated hydrocarbon group, substituted silyl group, alkoxy group or di-substituted amino group, and they may be the same or different. $G^+$ is an inorganic or organic cation, L is a neutral Lewis base, and $(L—H)^+$ is a Brønsted acid.).
(B) Organoaluminum Compound The organoaluminum compound (B) is an aluminum compound having a carbon-aluminum bond, and one or more of aluminum compounds selected from the following (B1) to (B3) are preferable.
(B1) An organoaluminum compound represented by the general formula $E^1{}_aAlZ_{3-a}$
(B2) Cyclic aluminoxane having a structure represented by the general formula $\{—Al(E^2)—O—\}_b$
(B3) Linear aluminoxane having a structure represented by the general formula $E^3\{—Al(E^3)—O—\}_cAlE^3{}_2$
(wherein, each of $E^1$, $E^2$ and $E^3$ is hydrocarbon group, and all $E^1$'s, all $E^2$'s and all $E^3$'s may be the same or different respectively. Z represents a hydrogen atom or halogen atom, and all Z's may be the same or different. a represents a number satisfying $0<a\leq3$, b is an integer of 2 or more, and c is an integer of 1 or more.).

The hydrocarbon group in $E^1$, $E^2$ or $E^3$ is preferably a hydrocarbon group having 1 to 8 carbon atoms, and more preferably an alkyl group.

Specific examples of the organoaluminum compound (B1) represented by the general formula $E^1{}_aAlZ_{3-a}$ include trialkylaluminums such as trimethylaluminum, triethylaluminum, tripropylaluminum, triisobutylaluminum, trihexylaluminum and the like; dialkylaluminum chlorides such as dimethylaluminum chloride, diethylaluminum chloride, dipropylaluminum chloride, diisobutylaluminum chloride, dihexylaluminum chloride and the like; alkylaluminum dichlorides such as methylaluminum dichloride, ethylaluminum dichloride, propylaluminum dichloride, isobutylaluminum dichloride, hexylaluminum dichloride and the like; dialkylaluminum hydrides such as dimethylaluminum hydride, diethylaluminum hydride, dipropylaluminum hydride, diisobutylaluminum hydride, dihexylaluminum hydride and the like; and so forth.

The trialkylaluminum is preferable, and triethylaluminum or triisobutylaluminum is more preferable.

Specific examples of $E^2$ and $E^3$ in (B2) cyclic aluminoxane having a structure represented by the general formula $\{—Al(E^2)—O—\}_b$ and (B3) linear aluminoxane having a structure represented by the general formula $E^3\{—Al(E^3)—O—\}_cAlE^3{}_2$ include alkyl groups such as a methyl group, ethyl group, n-propyl group, isopropyl group, n-butyl group, isobutyl group, n-pentyl group, neopentyl group and the like. b is an integer of 2 or more, c is an integer of 1 or more. Preferably, $E^2$ and $E^3$ represent a methyl group or isobutyl group, and b is 2 to 40 and c is 1 to 40.

The above-described aluminoxane is made by various methods. This method is not particularly restricted, and the aluminoxane may be produced according to a known method. For example, a solution prepared by dissolving a trialkylaluminum (for example, trimethylaluminum and the like) in a suitable organic solvent (benzene, an aliphatic hydrocarbon or the like) is allowed to contact with water to produce aluminoxane. Further, there is exemplified a method in which la trialkylaluminum (for example, trimethylaluminum and the like) is allowed to contact with a metal salt containing crystal water (for example, copper sulfate hydrate and the like) to produce aluminoxane.

(C) Boron Compound

As the boron compound (C), any of a boron compound (C1) represented by the general formula $BQ^1Q^2Q^3$, a boron compound (C2) represented by the general formula $G^+(BQ^1Q^2Q^3Q^4)^-$, and a boron compound (C3) represented by the general formula $(L—H)^+(BQ^1Q^2Q^3Q^4)^-$ is used.

In the boron compound (C1) represented by the general formula $BQ^1Q^2Q^3$, B is a boron atom in the trivalent valence state, $Q^1$ to $Q^3$ are a halogen atom, hydrocarbon group, halogenated hydrocarbon group, substituted silyl group, alkoxy group or di-substituted amino group, and they may be the same or different. $Q^1$ to $Q^3$ are preferably a halogen atom, hydrocarbon group having 1 to 20 carbon atoms, halogenated hydrocarbon group having 1 to 20 carbon atoms, substituted silyl group having 1 to 20 carbon atoms, alkoxy group having 1 to 20 carbon atoms or amino group having 2 to 20 carbon atoms, and more preferably, $Q^1$ to $Q^3$ are a halogen atom, hydrocarbon group having 1 to 20 carbon atoms, or halogenated hydrocarbon group having 1 to 20 carbon atoms. Further preferably, $Q^1$ to $Q^4$ are a fluorinated hydrocarbon group having 1 to 20 carbon atoms containing at least one fluorine atom, and particularly preferably, $Q^1$ to $Q^4$ are a fluorinated aryl group having 6 to 20 carbon atoms containing at least one fluorine atom.

Specific examples of the compound (C1) include tris (pentafluorophenyl)borane, tris(2,3,5,6-tetrafluorophenyl) borane, tris(2,3,4,5-tetrafluorophenyl)borane, tris(3,4,5-trifluorophenyl)borane, tris(2,3,4-trifluorophenyl)borane, phenylbis(pentafluorophenyl)borane and the like, and tris (pentafluorophenyl)borane is most preferable.

In the boron compound (C2) represented by the general formula $G^+(BQ^1Q^2Q^3Q^4)^-$, G+ is an inorganic or organic cation, B is a boron atom in the trivalent valence state, and $Q^1$ to $Q^4$ are as defined for $Q^1$ to $Q^3$ in the above-mentioned (C1).

Specific examples of the inorganic cation $G^+$ in a compound represented by the general formula $G^+(BQ^1Q^2Q^3Q^4)^-$ include a ferrocenium cation, alkyl-substituted ferrocenium cation, silver cation and the like, specific examples of the organic cation $G^+$ thereof include a triphenylmethyl cation and the like. $G^+$ is preferably a carbenium cation, and particularly preferably a triphenylmethyl cation. Examples of $(BQ^1Q^2Q^3Q^4)^-$ include tetrakis(pentafluorophenyl) borate, tetrakis(2,3,5,6-tetrafluorophenyl)borate, tetrakis(2,3,4,5-tetrafluorophenyl)borate, tetrakis(3,4,5-trifluorophenyl)borate, teterakis(2,3,4-trifluorophenyl) borate, phenyltris(pentafluorophenyl) borate, tetrakis(3,5-bistrifluoromethylphenyl)borate and the like.

As specific combination of them, ferroceniumtetrakis (pentafluorophenyl)borate, 1,1'-dimethylferroceniumtetrakis(pentafluorophenyl)borate, silvertetrakis(pentafluorophenyl)borate, triphenylmethyltetrakis(pentafluorophenyl)borate, triphenylmethyltetrakis(3,5-bistrifluoromethylphenyl) borate and the like are listed, and triphenylmethyltetrakis (pentafluorophenyl)borate is most preferable.

In the boron compound (C3) represented by the general formula $(L—H)+(BQ^1Q^2Q^3Q^4)^-$, L is a neutral Lewis base, $(L—H)^+$ is a Broensted acid, B is a boron atom in the trivalent valence state, and $Q^1$ to $Q^4$ are as defined for $Q^1$ to $Q^3$ in the above-mentioned Lewis acid (C1).

Specific examples of the Broensted acid (L—H)+in a compound represented by the general formula $(L—H)^+$ $(BQ^1Q^2Q^3Q^4)^-$ include a trialkyl-substituted ammonium, N,N-dialkylanilinium, dialkylammonium, triaryl phosphonium and the like, and as the $(BQ^1Q^2Q^3Q^4)^-$, the same compounds as described above are listed.

As specific combination of them, there are listed triethylammoniumtetrakis(pentafluorophenyl)borate, tripropylammoniumtetrakis(pentafluorophenyl)borate, tri(n-butyl)ammoniumtetrakis(pentafluorophenyl)borate, tri(n-butyl)ammoniumtetrakis(3,5-bistrifluoromethylphenyl) borate, N,N-dimethylaniliniumtetrakis(pentafluorophenyl) borate, N,N-diethylaniliniumtetrakis(pentafluorophenyl) borate, N,N-2,4,6-pentamethylaniliniumtetrakis (pentafluorophenyl)borate, N,N-dimethylaniliniumtetrakis (3,5-bistrifluoromethylphenyl)borate, diisopropylammoniumtetrakis(pentafluorophenyl)borate, dicyclohexylammoniumtetrakis(pentafluorophenyl)borate, triphenylphosphoniumtetrakis(pentafluorophenyl)borate, tri (methylphenyl)phosphoniumtetrakis(pentafluorophenyl) borate, tri(dimethylphenyl)phosphoniumtetrakis (pentafluorophenyl)borate and the like, and tri(n-butyl) ammoniumtetrakis(pentafluorophenyl)borate or N,N-dimethylaniliniumtetrakis(pentafluorophenyl)borate is most preferable.

In the present invention, the above-mentioned transition metal compound (A), and as the co-catalyst, the organic aluminum compound (B) and/or the above-mentioned compound (C) can be charged in any order in polymerization and used, alternatively, a reaction product obtained by previously contacting these compounds in any combination may also be used.

Regarding amounts of catalyst components used, it is desirable to use the components so that the molar ratio of organoaluminum compound (B)/transition metal compound (A) is usually from 0.1 to 10000, preferably from 5 to 2000, and the molar ratio of boron compound (C)/transition metal compound (A) is usually from 0.01 to 100, preferably from 0.5 to 10. Regarding the concentrations when catalyst components are used in the form of a solution, it is desirable to use the components so that the concentration of the transition metal compound (A) is usually from 0.0001 to 5 mmol/liter, preferably from 0.001 to 1 mmol/liter, the concentration of the organoaluminum compound (B) is usually from 0.01 to 500 mmol/liter, preferably from 0.1 to 100 mmol/liter in terms of an Al atom, and the concentration of the boron compound (C) is usually from 0.0001 to 5 mmol/liter, preferably from 0.001 to 1 mmol/liter.

As the olefin which can be applied in polymerization in the present invention, there can be used olefins having 2 to 20 carbon atoms, particularly, ethylene, α-olefins having 3 to 20 carbon atoms, diolefins having 4 to 20 carbon atoms, and the like, and also, 2 or more of olefins can be used simultaneously. Specific examples of the olefin include linear olefins such as ethylene, propylene, 1-butene, 1-pentene, 1-hexene, 1-heptene, 1-octene, 1-nonene, 1-decene and the like, branched olefins such as 3-methyl-1-butene, 3-methyl-1-pentene, 4-methyl-1-pentene, 5-methyl-1-hexene and the like, vinylcyclohexane and the like, but the scope of the present invention should not be limited to the above-mentioned compounds. Specific combinations of olefins in copolymerization, include ethylene and propylene, ethylene and 1-butene, ethylene and 1-hexene, ethylene and 1-octene, propylene and 1-butene, and the like, but the scope of the present invention should not be limited to these combinations.

The present invention can be applied effectively for production of copolymers of particularly ethylene with other α-olefin, specifically, propylene, 1-butene, 4-methyl-1-pentene, 1-hexene, 1-octene or the like.

The polymerization process also should not be limited particularly, and for example, solvent polymerization or slurry polymerization using as a solvent an aliphatic hydrocarbon such as butane, pentane, hexane, heptane, octane or the like, an aromatic hydrocarbon such as benzene, toluene or the like, or a halogenated hydrocarbon such as methylene dichloride or the like, gas-phase polymerization in a gaseous monomer, or the like can be used, and it is possible to select any of continuous polymerization and batch-wise polymerization.

The polymerization temperature can be in the range from −50 to 250° C., and particularly, the range from −20 to 100° C. is preferable, and the polymerization pressure is preferably from normal pressure to 60 kg/cm$^2$ G. The polymerization time is appropriately determined depending generally on the kind of the intended polymer, and the reaction apparatus, and can be in the range from 1 minute to 20 hours. Further, a chain transfer agent such as hydrogen or the like can also be added in the present invention to regulate the molecular weight of a polymer

EXAMPLE

The following examples and comparative examples will illustrate the present invention further in detail below, but do not limit the scope of the present invention.

Properties of polymers in the examples were measured according to the following methods.

(1) Intrinsic viscosity [η]: It was measured using a Ubbellohde viscometer at 135° C. in a tetralin solution.

(2) α-Olefin unit content in copolymer: It was measured by the characteristic absorptions of ethylene and α-olefin using an infrared spectrophotometer (IR-810 manufactured by Nippon Bunko Kogyo Ltd.), and represented as the number of short chain branching (SCB) per 1000 carbons.

(3) Melting point of polymer: It was measured by using Seiko SSC-5200 under the following conditions.
Raising temperature: from 40° C. to 150° C. (10° C./min.); kept for 5 minutes
Cooling: from 150° C. to 10° C. (5° C./min.); kept for 10 minutes
Measurement: from 10 to 160° (5° C./min.)

(4) Molecular weight and molecular weight distribution: The molecular weight was measured by using gel permeation chromatograph (150, C manufactured by Waters) under the following conditions.
Column: TSK gel GMH-HT
Measurement temperature: set at 145° C.
Measurement concentration: 10 mg/10 ml-orthodichlorobenzene The molecular weight distribution was evaluated as the ratio (Mw/Mn) of the weight-average molecular weight to the number-average molecular weight.

Example 1

(1) Synthesis of N-Trimethylsilyl-tri-tert-butylphosphineimine

Into a 100 ml four-necked flask equipped with a stirrer and cooling apparatus was charged 44.8 g (221 mmol) of tri-tert-butylphosphine and 27.8 g (242 mmol) of trimethylsilylazide under nitrogen atmosphere. This solution was heated from 100° C. to 120° C., and stirred from 1.5 hours. Then, 6 g (52 mmol) of trimethylsilylazide was added, and the mixture was further stirred at 125° C. to 130° C. for 1 hour. Thus obtained reaction solution was cooled, and 100 ml of dehydrated acetonitrile was added at 60° C., and the mixture was cooled to room temperature. To the resulted slurry was added further 420 ml of dehydrated acetonitrile, and the mixture was heated to 70° C. to give a solution. This solution was left to cool to room temperature, and allowed to stand still over night to obtain a colorless needle-like crystal. This was filtrated, and further washed with 50 ml of dehydrated acetonitrile, and dried to obtain 47.8 g (165 mmol) of N-trimethylsilyl-tri-tert-butylphosphineimine in the form of a colorless needle-like crystal. The yield was 75%.

$^1$H-NMR(CDCl$_3$): d-0.20 (2,9H), 1,28 (d, 27H, J=12 Hz) $^{31}$P-NMR(CDCl$_3$): d 32.7

(2) Synthesis of (Cyclopentadienyl)(tri-tert-butylphosphineimine)titanium Dichloride In a 100 ml flak equipped with a stirrer, 5.08 g (23.1 mmol) of cyclopentadienyltitanium dichloride was dissolved in 100 ml of toluene under nitrogen atmosphere. To this was added a solution prepared by dissolving 7.50 g (26.0 mmol) of N-triemthylsilyl-tri-tert-butylphosphineimine synthesized in (1) above in 30 ml of toluene, slowly at room temperature. The resulted orange color solution was stirred at room temperature for one day to obtain a suspension which was filtrated through Celite, and the filtrate was collected, condensed and cooled for crystallization to give 6.70 g (16.8 mmol) of (cyclopentadienyl)(tri-tert-butylphosphineimine) titanium dichloride in the form of a yellow plate-like crystal. The yield was 73%.

$^1$H-NMR(CDCl$_3$): d 1.54 (d, 27H, J=13.9 Hz), 6.48 (s, 5H) $^{31}$ P-NMR(CDCl$_3$): d 48.3

(3) Synthesis of (Cyclopentadienyl)(tri-tert-butylphosphineimine)(1,4-diphenylbutadiene) titanium In a 100 ml flak equipped with a stirrer, 1.00 g (2.50 mmol) of (cyclopentadienyl)(tri-tert-butylphosphineimine) titanium dichloride synthesized in (2) above and 0.875 g (2.50 mmol) of 1,4-diephnylbutadiene were dissolved in 30 ml of toluene under nitrogen atmosphere. To this yellow solution was added 3.4 ml of a 1.55 mol/liter n-butyllithium/n-hexane solution at room temperature dropwise. This solution was heated under ref lux for 2 hours, then, filtrated through Celite, and further condensed to 20 ml, then, heated to give a dark black solution. This solution was left to cool to room temperature, then, allowed to stand still at −20° C. over night to give a dark bright needle-like crystal. This crystal was filtrated and washed with 5 ml of n-pentane three times and dried to obtain 0.88 g (1.65 mmol) of (cyclopentadienyl)(tri-tert-butylphosphineimine)(1,4-diphenylbutadiene)titanium in the form of a dark bright needle-like crystal. The yield was 66%.

$^1$H-NMR(C$_6$D$_6$): d 1.14 (d, 27H, J=13.2 Hz), 4.04 (s, 2H), 5.53 (s, 2H), 6,15 (s, 5H), 6.93–7.59 (m, 10H)

Example 2

An autoclave having an inner volume of 0.4 liter equipped with a stirrer was dried in vacuo, purged with argon, then, 190 ml of toluene was charged as a solvent, and 10 ml of 1-hexene was charged as an α-olefin, and the reaction vessel was heated up to 80° C. After the heating, ethylene was fed while controlling the ethylene pressure at 6 kg/cm$^2$, and after the system was stabilized, 1.0 mmol (mol number in terms of an aluminum atom; hereinafter the same) of a solution of methylisobutylaluminoxane in toluene (MMAO 3A, manufactured by TOSOH-AKZO, hereinafter, simply abbreviated as "MMAO") was charged, subsequently, 0.5 μmol of (cyclopentadienyl)(tri-tert-butylphosphineimine)(1,4-diphenylbutadiene)titanium synthesized in the above-mentioned Example 1 (3) was charged. Polymerization was conducted for 60 minutes while controlling the temperature at 80° C. The temperature in the polymerization chamber increased by 8.0° C. by the initial heat generation in this procedure.

As a result of the polymerization, a copolymer of ethylene with 1-hexene having SCB of 23.1, [η]=5.24 dl/g, molecular weight (Mw) of $4.9 \times 10^5$, molecular weight distribution (Mw/Mn) of 2.8 and melting temperature of 107.7° C. was produced at a rate of $2.3 \times 10^7$ g per 1 hour per 1 mol of a titanium atom.

Example 3

An autoclave having an inner volume of 0.4 liter equipped with a stirrer was dried in vacuo, purged with argon, then, 190 ml of toluene was charged as a solvent, and 10 ml of 1-hexene was charged as an α-olefin, and the reaction vessel was heated up to 80° C. After the heating, ethylene was fed while controlling the ethylene pressure at 6 kg/cm$^2$, and after the system was stabilized, 0.25 mmol of triisobutylaluminum was charged, subsequently, 0.5 μmol of (cyclopentadienyl)(tri-tert-butylphosphineimine)(1,4-diphenylbutadiene)titanium was charged, then, 1.5 μmol of triphenylmethyltetrakis(pentafluorophenyl)borate was charged. Polymerization was conducted for 60 minutes while controlling the temperature at 80° C. The temperature in the polymerization chamber increased by 7.0° C. by the initial heat generation in this procedure.

As a result of the polymerization, a copolymer of ethylene with 1-hexene having SCB of 25.2, [η] of 7.01 dl/g, molecular weight (Mw) of $5.3 \times 10^5$, molecular weight distribution (Mw/Mn) of 3.3 and melting temperature of 106.6° C. was produced at a rate of $2.4 \times 10^7$ g per 1 hour per 1 mol of a titanium atom.

Comparative Example 1

An autoclave having an inner volume of 0.4 liter equipped with a stirrer was dried in vacuo, purged with argon, then, 190 ml of toluene was charged as a solvent, and 10 ml of 1-hexene was charged as an α-olefin, and the reaction vessel was heated up to 80° C. After the heating, ethylene was fed while controlling the ethylene pressure at 6 kg/cm$^2$, and after the system was stabilized, 2.0 mmol of MMAO was charged, subsequently, 1.0 μmol of (cyclopentadienyl) (tri-tert-butylphosphineimine)titanium dichloride synthesized in the above-mentioned Example 1 (2) was charged. Polymerization was conducted for 60 minutes while controlling the temperature at 80° C. The temperature in the polymerization chamber increased by 14.8° C. by the initial heat generation in this procedure.

As a result of the polymerization, a copolymer of ethylene with 1-hexene having a SCB of 25.8, [η] of 5.23 dl/g, molecular weight (Mw) of $4.3 \times 10^5$, molecular weight distribution (Mw/Mn)=3.7 and melting temperature of 109.6° C. was produced at a rate of $5.5 \times 10^6$ g per 1 hour per 1 mol of a titanium atom.

Comparative Example 2

An autoclave having a content volume of 0.4 liter equipped with a stirrer was dried in vacuo, purged with argon, then, 190 ml of toluene was charged as a solvent, and 10 ml of 1-hexene was charged as an α-olefin, and the reaction vessel was heated up to 80° C. After the heating, ethylene was fed while controlling the ethylene pressure at 6 kg/cm and after the system was stabilized, 0.50 mmol of triisobutylaluminum was charged, subsequently, 1.0 μmol of (cyclopentadienyl)(tri-tert-butylphosphineimine)titanium dichloride was charged, then, 3.0 μmol of triphenylmethyltetrakis(pentafluorophenyl)borate was charged. Polymerization was conducted for 60 minutes while controlling the temperature at 80° C. The temperature in the polymerization chamber increased by 16.8° C. by the initial heat generation in this procedure.

As a result of the polymerization, a copolymer of ethylene with 1-hexene having a SCB of 24.2, [η] of 4.88 dl/g, molecular weight (Mw) of $3.8 \times 10^5$, molecular weight distribution (Mw/Mn) of 2.6 and melting temperature of 109.9° C. was produced at a rate of $7.9 \times 10^6$ g per 1 hour per 1 mol of a titanium atom.

According to the present invention, as described above in detail, a transition metal compound useful as an addition polymerization catalyst component which can manifest high activity, an addition polymerization catalyst component composed of this transition metal compound, an addition polymerization catalyst having high activity obtained by using this transition metal compound, and an efficient method for producing an olefin polymer using this addition polymerization catalyst are provided.

What is claimed is:

1. A transition metal compound obtained by reacting a transition metal compound (a) represented by the following general formula (1)

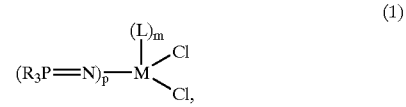

wherein, M represents a titanium atom, zirconium atom or hafnium atom; L represents a group having an aromatic π electron; R represents a hydrogen atom, alkyl group, aralkyl group, aryl group or substituted silyl group, all R's may be the same or different; p is 1 or 2; m is 0 or 1; and the sum of p and m is 2, with a conjugated diene (b) selected from the group consisting of 2,2,7,7-tetramethyl-3,6-octadiene, 2,4,5,7-tetramethyl-3,5-octadiene, 1,4-diphenylbutadiene and 2,3-diphenylbutadiene in the presence of a compound (c) selected from the group consisting of alkyllithiums, alkali metals, alkali metal hydrides and Grignard compounds.

2. A transition metal compound represented by the following general formula (2):

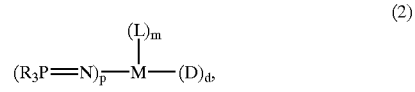

wherein, M represents a titanium atom, zirconium atom or hafnium atom; L represents a group having an aromatic π electron and is connected to M via the π electron; D represents a conjugated diene selected from the group consisting of 2,2,7,7-tetramethyl-3,5-octadiene, 2,4,5,7-tetramethyl-3,5-octadiene, 1,4-diphenylbutadiene and 2,3-diphenylbutadiene; R represents a hydrogen atom, alkyl group, aralkyl group, aryl group or substituted silyl group, and all R's may be the same or different; d is 1 or 2; p is 1 or 2, m is 0 or 1; and the sum of p and m is 2.

3. The transition metal compound according to claim 1, wherein the compound (b) is 1,4-diphenylbutadiene.

4. The transition metal compound according to claim 2, wherein D in the general formula is 1,4-diphenylbutadiene.

* * * * *